(12) United States Patent
Ulfarsson et al.

(10) Patent No.: US 8,721,660 B2
(45) Date of Patent: May 13, 2014

(54) STEREOTACTIC THERAPY SYSTEM

(75) Inventors: Elfar Ulfarsson, Reykjavík (IS); Anders Nordell, Täby (SE); Bo Nordell, Täby (SE)

(73) Assignee: Karolinska Institutet Innovations AB, Stockholm (SE)

( * ) Notice: Subject to any disclaimer, the term of this patent is extended or adjusted under 35 U.S.C. 154(b) by 609 days.

(21) Appl. No.: 12/668,019

(22) PCT Filed: Jul. 7, 2008

(86) PCT No.: PCT/EP2008/058800
§ 371 (c)(1),
(2), (4) Date: Oct. 4, 2010

(87) PCT Pub. No.: WO2009/007347
PCT Pub. Date: Jan. 15, 2009

(65) Prior Publication Data
US 2011/0098722 A1    Apr. 28, 2011

(30) Foreign Application Priority Data

Jul. 6, 2007 (WO) ................. PCT/EP2007/056910

(51) Int. Cl.
*A61B 19/00* (2006.01)
(52) U.S. Cl.
USPC ......................... 606/130; 600/426; 600/429
(58) Field of Classification Search
USPC ............. 606/1, 130; 600/426, 429, 437, 427, 600/423, 449, 407, 410, 414, 424, 431, 600/416; 378/162, 205, 20, 204; 382/154
See application file for complete search history.

(56) References Cited

U.S. PATENT DOCUMENTS

| | | | | |
|---|---|---|---|---|
| 5,394,457 A | * | 2/1995 | Leibinger et al. | 378/162 |
| 5,634,929 A | | 6/1997 | Misko et al. | |
| 6,073,044 A | * | 6/2000 | Fitzpatrick et al. | 600/426 |
| 6,419,680 B1 | | 7/2002 | Cosman et al. | |
| D527,820 S | * | 9/2006 | Solar et al. | D24/140 |

(Continued)

FOREIGN PATENT DOCUMENTS

| | | |
|---|---|---|
| EP | 0 427 358 A1 | 5/1991 |
| EP | 0 591 712 A1 | 4/1994 |
| WO | WO 99/15097 A2 | 4/1999 |
| WO | WO 2005/120380 A1 | 12/2005 |

*Primary Examiner* — Darwin Erezo
*Assistant Examiner* — Katrina Stransky
(74) *Attorney, Agent, or Firm* — Inskeep IP Group, Inc.

(57) ABSTRACT

A fiducial marker system (210*a-c*) comprises a first unit and a second unit. The first unit is patient affixable and comprises a partly spherical inner surface having a first center point that is adapted to receive a touch probe measurement head for measuring the spatial position of the center point. The second unit is releasably attachable to an outer surface of the first unit, and has a second center point, wherein the first center point and the second center point are substantially identical when the second unit is attached to the first unit. For stereotactic therapy, a patient is imaged with the first and second unit assembled. Then the second unit is detached. A stereotactic frame (300) is attached to the first units via arms. Thus frameless imaging is provided in a frame based stereotactic surgery system with high precision. Repeated assembly of the frame (300) to the first units, remaining in the patient, provides advantageous fractionized stereotactic radiotherapy.

6 Claims, 16 Drawing Sheets

(56) References Cited

U.S. PATENT DOCUMENTS

| | | |
|---|---|---|
| 2002/0042619 A1 | 4/2002 | Dominguez et al. |
| 2002/0095081 A1 | 7/2002 | Vilsmeier |
| 2004/0030237 A1* | 2/2004 | Lee et al. .................. 600/414 |
| 2004/0167393 A1* | 8/2004 | Solar et al. ................ 600/414 |
| 2010/0298846 A1* | 11/2010 | Kao et al. .................. 606/130 |

* cited by examiner

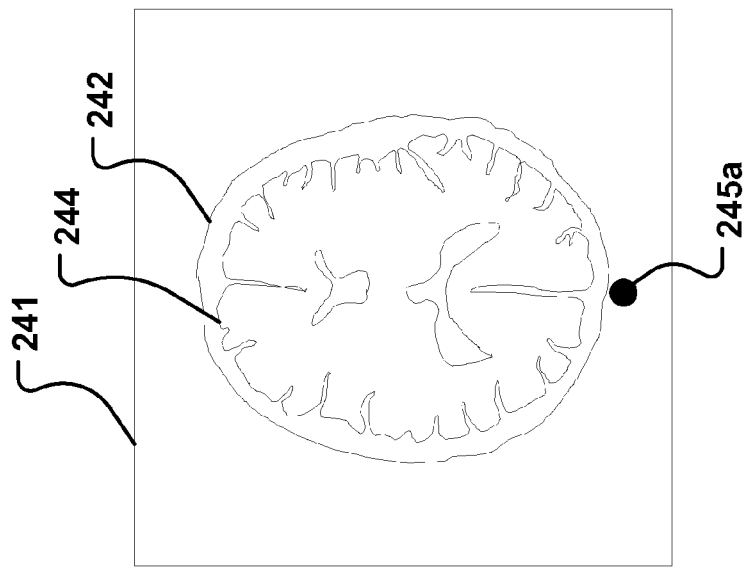
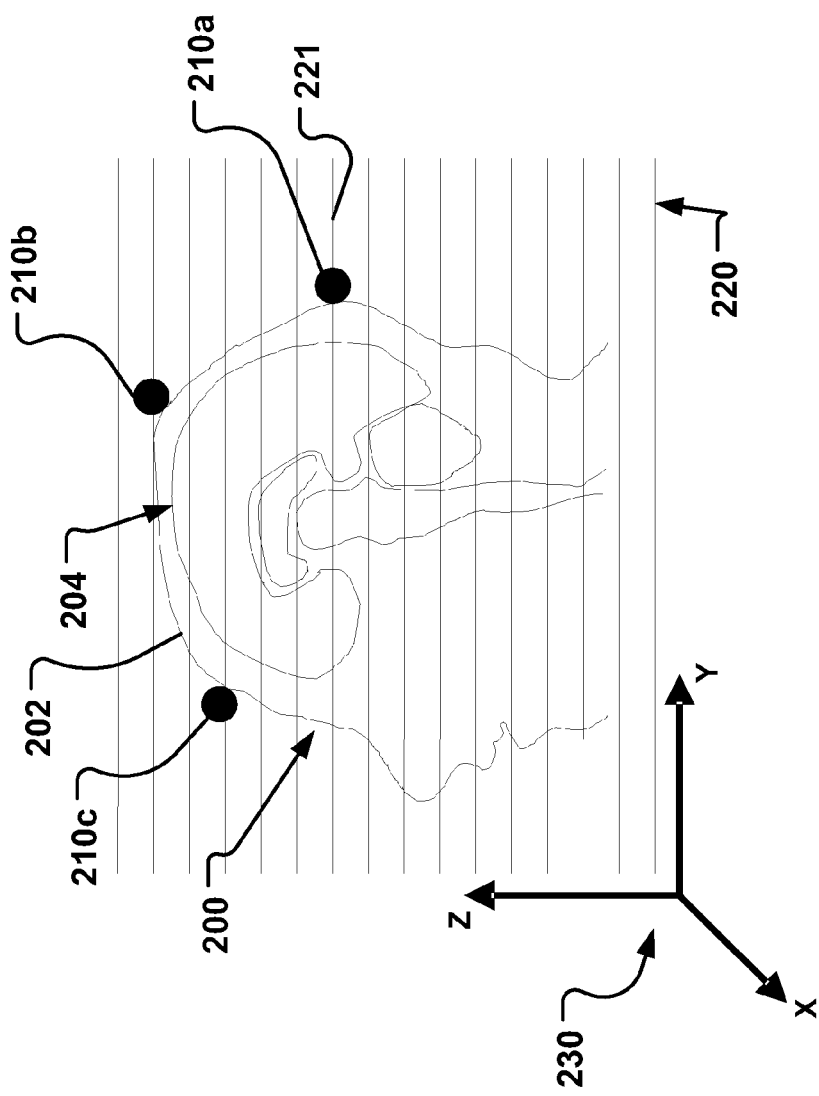

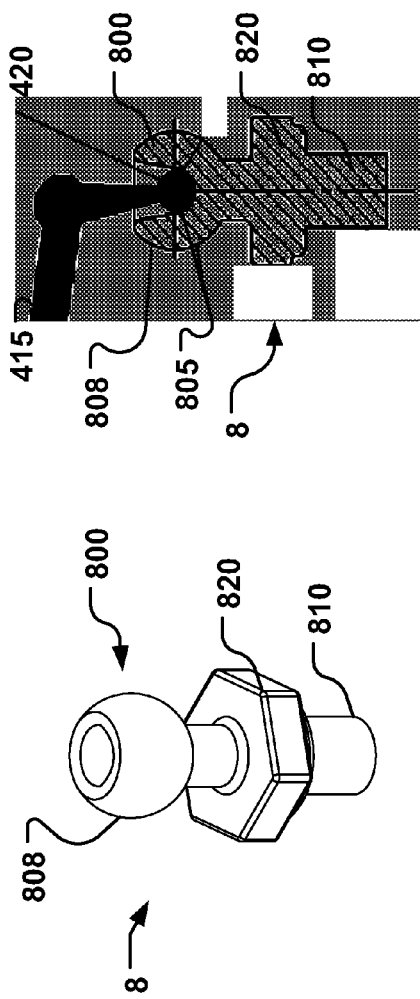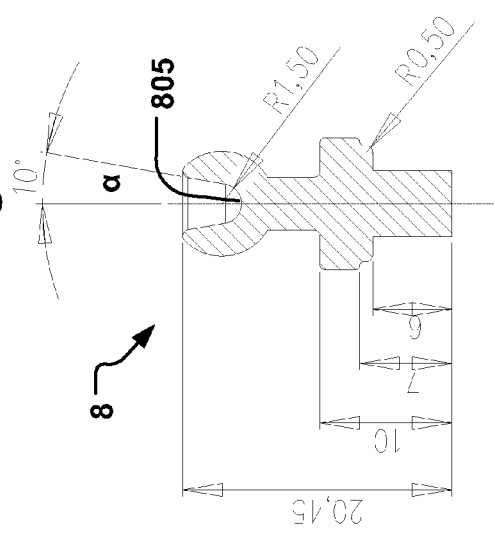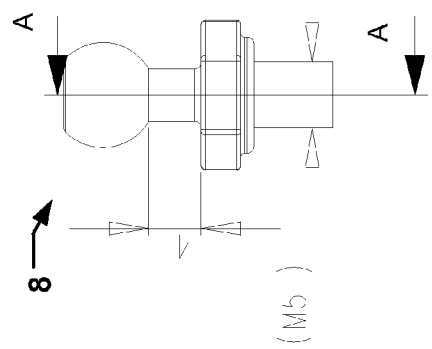

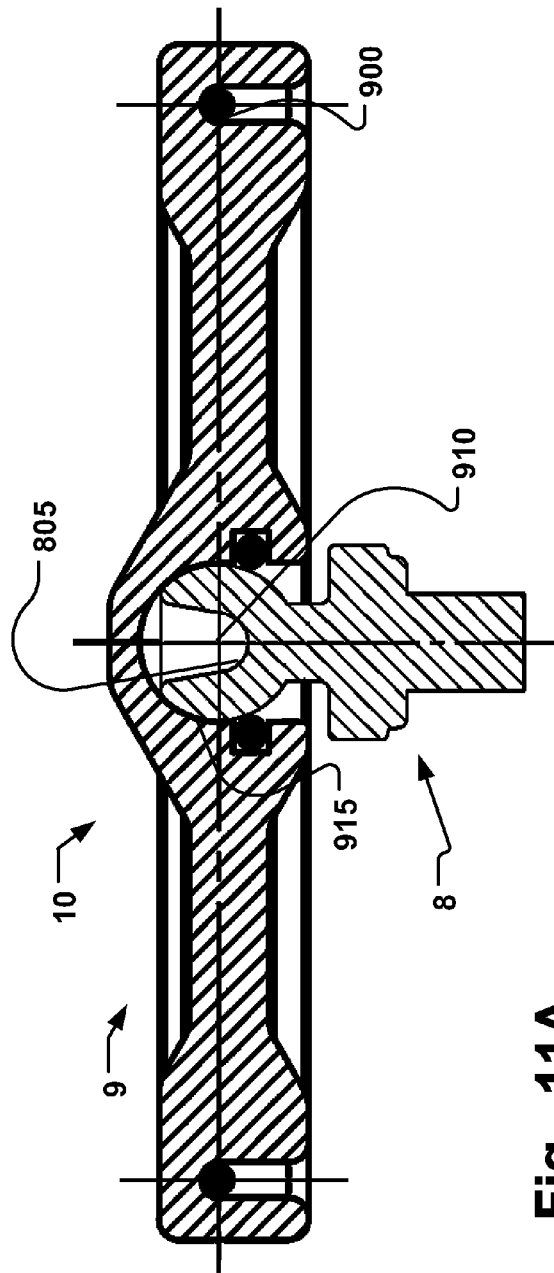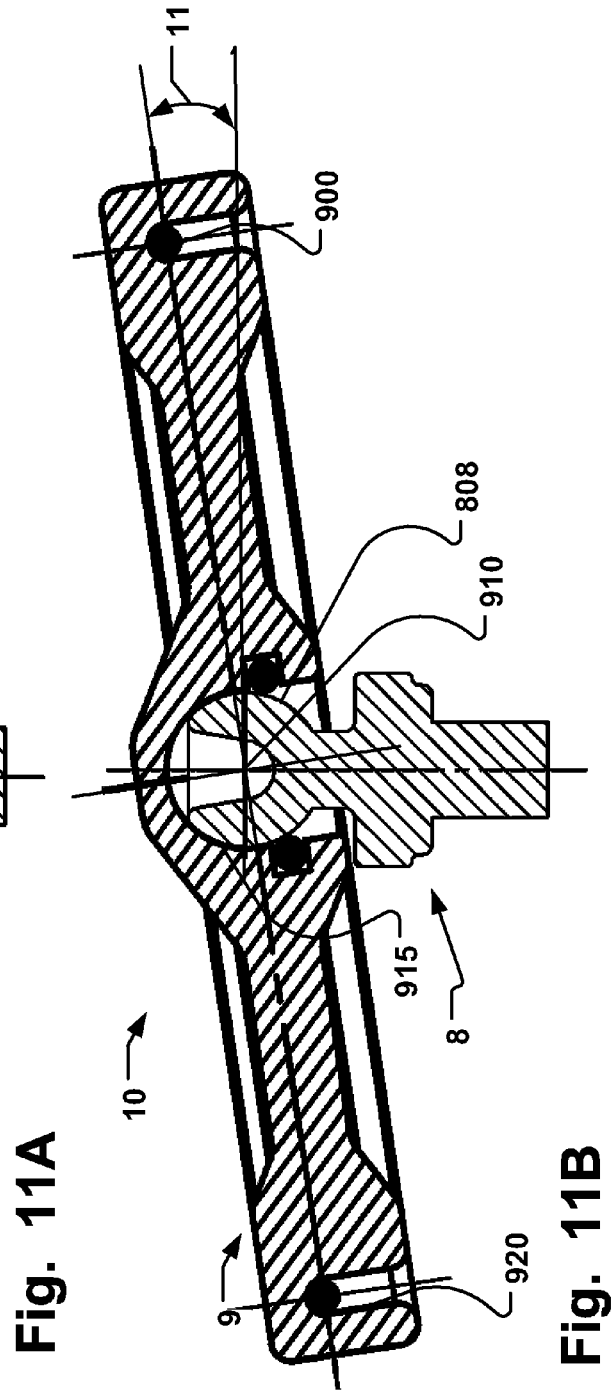

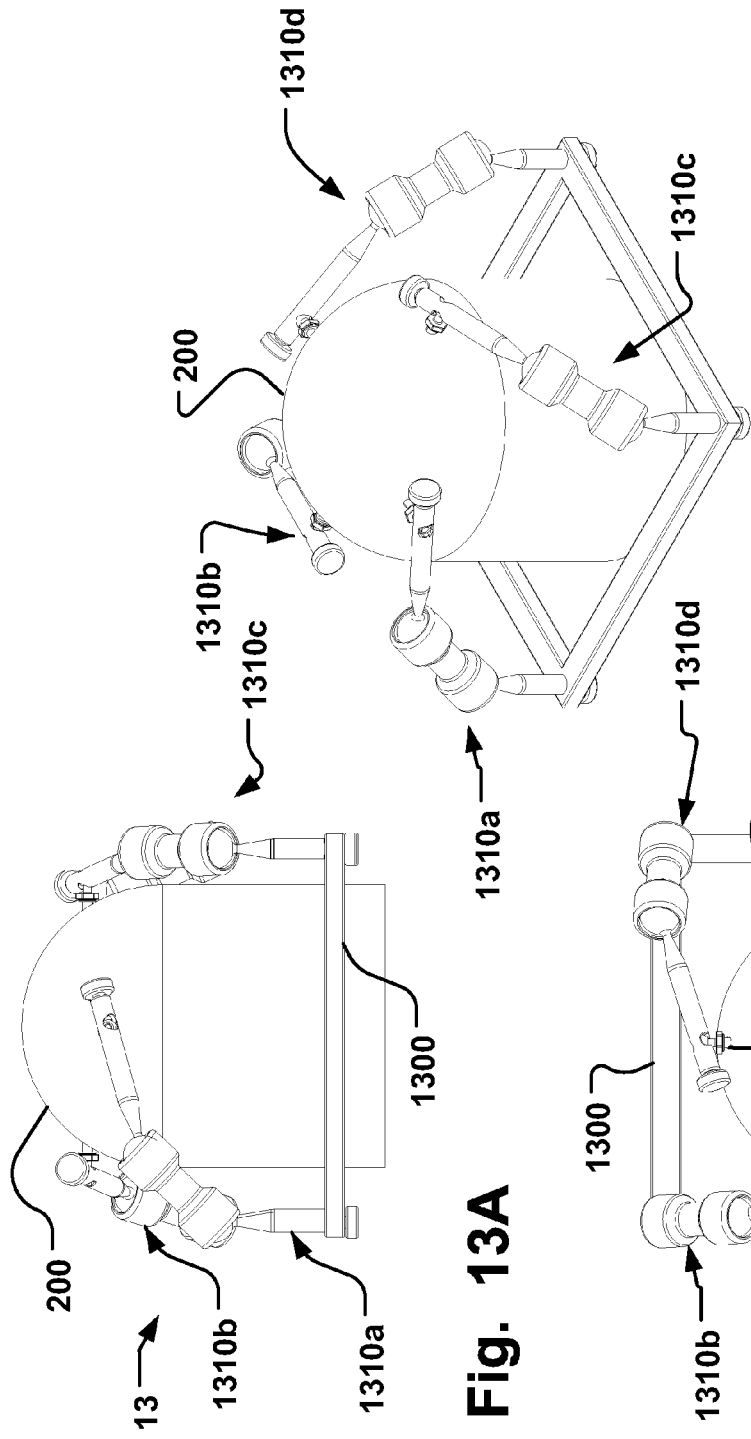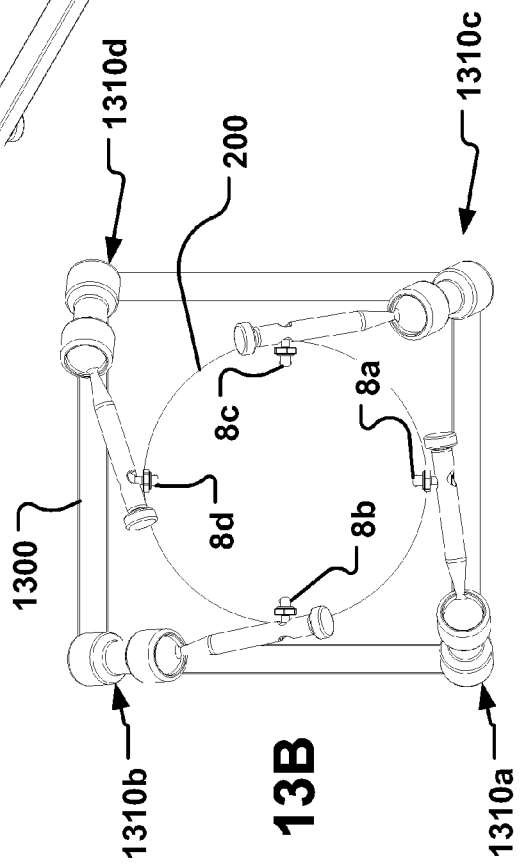

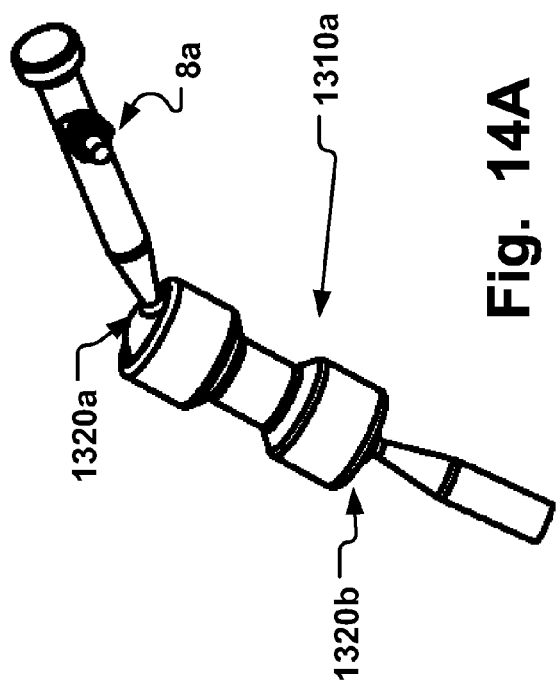
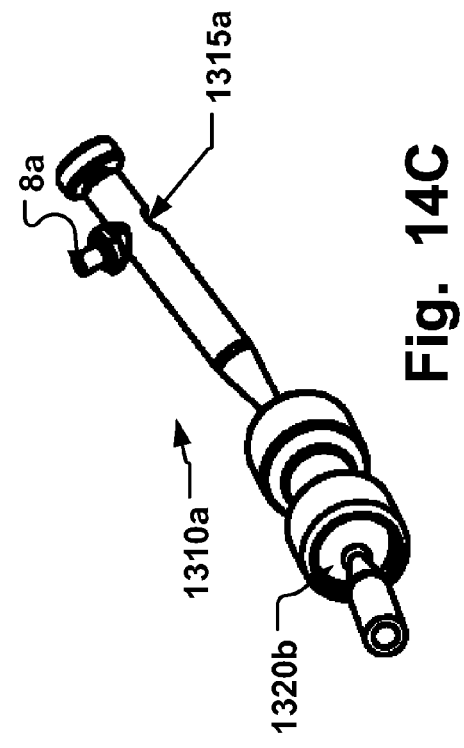
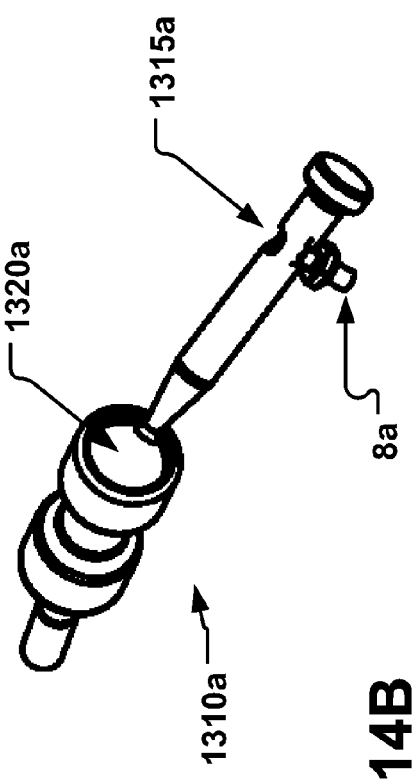

STEREOTACTIC THERAPY SYSTEM

RELATED APPLICATIONS

This application claims priority to International Patent Application No. PCT/EP2008/05880, International Filing Date 7 Jul. 2008, entitled Stereotactic Therapeutic System, and to International Patent Application No. PCT/EP2007/056910, International Filing Date 6 Jul. 2007 entitled Stereotactic Surgery System, both of which are hereby incorporated herein by reference.

FIELD OF THE INVENTION

The present invention pertains to the medical diagnostic and stereotactic therapeutic arts.

BACKGROUND OF THE INVENTION

In the field of medicine where treatment of a disease depends on inactivation or destruction of a certain tissue or biological target, the need of a highly focused treatment energy is important to spare the surrounding healthy tissues. The most accurate systems used for this purpose today rely on an ultimate fixation of a stereotactic system to the target body.

Stereotactic framebased radiosurgery uses sophisticated computerized imaging to provide data for an area of treatment in a patient body. Precisely targeting of narrow beams of radiation to such areas of treatment is based on a stereotactic frame attached to the patient. Thus it is for instance possible to effectively destroy small tumors or close down abnormal blood vessels. Stereotactic surgery, uses equivalent methods to define the target of invasive procedures. These techniques require targeting accuracies down to one millimeter or less. For instance in stereotactic radiosurgery or radiotherapy of the brain, very precise delivery of radiation to such a small volume of the brain, e.g. where a tumor is located, is provided, while sparing of the surrounding normal brain. This minimizes the effect of the radiation on the normal brain and reduces the risk of side effects.

For instance, U.S. Pat. No. 5,681,326 or U.S. Pat. No. 5,634,929 disclose stereotactic frame systems that benefits from a tight fixation of a mechanical frame to an anatomically fixed bone structure of the patient, which defines a stereotactic coordinate system. With the frame as reference, any point in three dimensions can be defined with high precision. Known systems use such a mechanical frame both during preoperative imaging and during surgery subsequent a planning thereof based on the imaging. However, the frame thus remains attached to the patient over a long period of time, which is inconvenient for the patient.

However, registering the physical space with the image space is difficult, in particular if high precision is required for the treatment of small areas in the imaged patient body, e.g. in the millimeter range.

Furthermore, when the imaging modality used to obtain the patient data for presurgical planning is a magnetic resonance imager (MRI) in conjunction with a frame based stereotactic system, one or more of the following issues may be taken into consideration. The physical size of the mechanical frame may not allow the operator to choose a receiver coil of the MRI freely. Modern scanners use receiver coils that are tightly fit to the surface of the patient in order to optimize the imaging procedure. Therefore, a patient having a stereotactic frame affixed, may not fit into a MRI.

Furthermore, the material of the mechanical frame may affect the performance of an imager, such as a MRI. Hence certain image procedures may be prohibited, for example diffusion weighted magnetic resonance imaging.

Moreover, in case the material of the mechanical frame is conducting, the frame might increase the geometrical distortions and/or increase the risk of local heating of the patient in the areas where the mechanical frame is fixated.

Also, for certain treatment modalities such as radiation based, the optimal treatment goal is often best met by repeated treatment sessions over a certain time period of days or weeks. To gain an ultimate stereotactic treatment accuracy with repeated treatment the frame has to remain fixed to the patient body during the whole treatment period or alternatively be removed after each treatment session and relocated/fixed again before the next treatment session, which is cumbersome both for the patient and the health care system.

The patient positioning in frame based stereotactic therapy relies on a mounted mechanical frame. The frame has to remain attached to the patient during imaging and therapy. Thus, when fractioning the treatment into a plurality of treatment fractions, the frame needs to be mounted to the patient for a long time. Alternatively, a new set of images and target planning has to be performed before each treatment fraction. This makes such a procedure expensive, time consuming, and little patient friendly.

Thus, there is a need for an improved stereotactic therapy system and/or method.

Hence, an improved stereotactic therapy system and/or method would be advantageous, and in particular a stereotactic therapy system allowing for increased flexibility, cost-effectiveness, accuracy, patient friendliness, and/or patient safety, would be advantageous.

SUMMARY OF THE INVENTION

Accordingly, embodiments of the present invention preferably seek to mitigate, alleviate or eliminate one or more deficiencies, disadvantages or issues in the art, such as the above-identified, singly or in any combination by providing a fiducial marker system, a stereotactic frame, a stereotactic system, method of providing data in a stereotactic system, a computer program, a medical workstation, and a method for performing stereotactic surgery, according to the appended patent claims.

A stereotactic treatment system is described, which enables frame less stereotactic imaging and relocation of a stereotactic frame/construction for the purpose of repeated treatment session of certain targets in the body.

According to a first aspect of the invention, a fiducial marker system is provided that comprises a first unit and a second unit. The first unit is patient affixable and configured to be secured in relation to a boney anatomical structure of a patient. The first unit comprises a partly spherical inner surface having a first center point that is adapted to receive a touch probe measurement head for measuring the spatial position of the first center point, and an outer surface. The second unit is releasably attachable to the outer surface of the first unit, and has a second center point, wherein the first center point and the second center point are substantially identical when the second unit is attached to the first unit. The outer surface of the first unit is configured to releasably receive the second unit. The outer surface of the first unit is configured to be releasably attached to an arm when the second unit is detached from the first unit. In this manner the first unit is configured to provide a fixed spatial relation between the patient and other equipment via the arm.

According to a second aspect of the invention, a stereotactic frame is provided. The stereotactic frame comprises a base unit and a plurality of arms mounted to the base unit. A mounting unit is provided at an end portion of the arms that is arranged for affixing each of the arms, and thus the stereotactic frame, to an outer surface of patient affixable first fiducial marker units of a fiducial marker system, such as the fiducial marker system of the first aspect of the invention. In this manner the base unit of the stereotactic frame has a spatial relationship to the first fiducial marker units and thus, when the first fiducial marker units are secured in relation to a boney anatomical structure of a patient, a fixed spatial relationship to the patient.

According to a third aspect of the invention, a stereotactic system is provided that comprises at least three fiducial markers according to the first aspect of the invention, and a stereotactic frame according to the second aspect of the invention, attachable to the fiducial markers via arms.

According to a fourth aspect of the invention, a method of providing data in a stereotactic therapy system according the third aspect of the invention is provided. The method comprises frameless imaging using fiducial markers according to the first aspect of the invention, and subsequent virtual planning of a stereotactic therapy. The virtually planned stereotactic therapy comprises a reference based on the stereotactic frame according to the second aspect of the invention affixed to the fiducial markers.

An anchoring unit of the fiducial markers remains attached to the patient during imaging and subsequent therapy. During imaging a second unit may be attached to the anchoring unit for improving accuracy of detecting a point in space of the fiducial marker. For therapy, the second unit is removed. The stereotactic frame is attached to the anchoring unit of the fiducial markers via arms. After a therapy session, the frame is removed from the anchoring units and patient. The anchoring unit may be left in the patient for a subsequent therapy session at a later point in time. During the subsequent therapy session the frame is re-attached to the anchoring units, which have remained in the patient in the meanwhile.

According to a fifth aspect of the invention, a computer program for processing by a computer is provided. The computer program comprises a first code segment for providing data in a stereotactic therapy system according to the third aspect of the invention comprising a code segment for frameless imaging using a fiducial marker system according to the first aspect of the invention; and a second code segment for subsequent virtual planning of a stereotactic therapy, the virtually planned stereotactic therapy comprising a reference based on the stereotactic frame according to the second aspect of the invention affixed to the fiducial markers.

According to a sixth aspect of the invention, a medical workstation is provided for performing the method according to the fourth aspect of the invention by running the computer program according to the fifth aspect of the invention.

According to yet a further aspect of the invention a method is provided for performing stereotactic therapy using the stereotactic frame system according to the second aspect of the invention. The method comprises performing stereotactic therapy based on a virtual planning performed by the method of the fourth aspect of the invention. The stereotactic therapy may be performed repeatedly as fractionized stereotactic radiotherapy, wherein anchoring units of the fiducial marker system remain affixed to the patient between therapy sessions and only the frame is attached/re-attached between sessions.

Further embodiments of the invention are defined in the dependent claims, wherein features for the second and subsequent aspects of the invention are as for the first aspect mutatis mutandis.

Some embodiments of the present invention provide for overcoming the issues and drawbacks associated with the imaging procedure in a frame based stereotactic system, while keeping the benefits of the frame in the surgical procedure.

Some embodiments of the invention provide for a user to perform diagnostic imaging using a frameless stereotactic reference system and then migrate this frameless stereotactic reference system into a frame based stereotactic system in order to perform stereotactic therapy.

The invention is of particular interest for a user that already is using a frame based stereotactic surgery system and wants to improve the system, e.g. the efficiency of the system, patient comfort, and/or patient throughput.

Some embodiments of the invention also provide for treatments to be fractionated, meaning that the treatment can be started, stopped and at a later time resumed. The user may perform diagnostic imaging using a frameless stereotactic reference system and then migrate to a frame based stereotactic system. If needed, the frame may then be removed and repositioned onto the patient, using the same frameless reference. This provides for time- and cost-efficient therapy. Moreover, this is less cumbersome for the patient.

Some embodiments provide for improved fractionated stereotactic radiosurgery or radiotherapy. This provides for instance an advantageous therapeutic treatment of intracranial lesions.

It should be emphasized that the term "comprises/comprising" when used in this specification is taken to specify the presence of stated features, integers, steps or components but does not preclude the presence or addition of one or more other features, integers, steps, components or groups thereof.

BRIEF DESCRIPTION OF THE DRAWINGS

These and other aspects, features and advantages of which embodiments of the invention are capable of will be apparent and elucidated from the following description of embodiments of the present invention, reference being made to the accompanying drawings, in which

FIGS. 2A and 2B are schematic illustrations of acquisition of a three dimensional (3D) image patient data in a slice based image system and the use of patient fiducial markers in the 3D image coordinate system;

FIGS. 8A to 8D are schematic illustrations of a first, patient affixable, unit of a fiducial marker having two separable units, in the form of a fiducial cup;

FIGS. 11A and 11B are sectional views of the fiducial marker, when the two units thereof are assembled, with the fiducial cup in two different orientations, respectively;

FIGS. 13A, 13B, 13C are schematic illustrations of an embodiment of a stereotactic frame, which is affixable at the patient affixable fiducial cups;

FIGS. 14A, 14B, and 14C are schematic illustrations of adjustable arms of the stereotactic frame of FIGS. 13A-13C;

DESCRIPTION OF EMBODIMENTS

Figure 1:
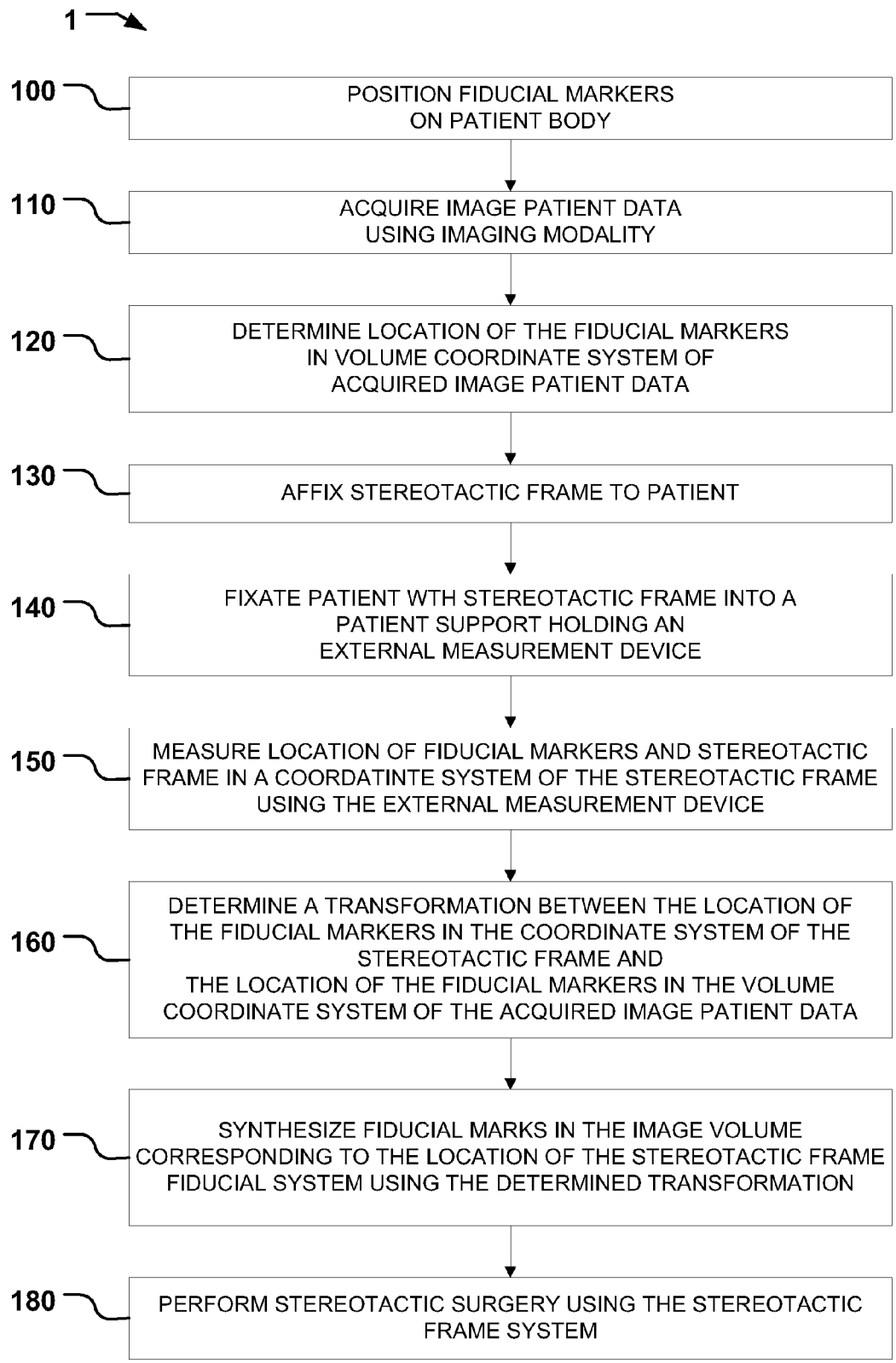
FIG. 1 is a flow chart illustrating an embodiment of a method of frameless imaging in a frame based surgical system.
Figure 3:
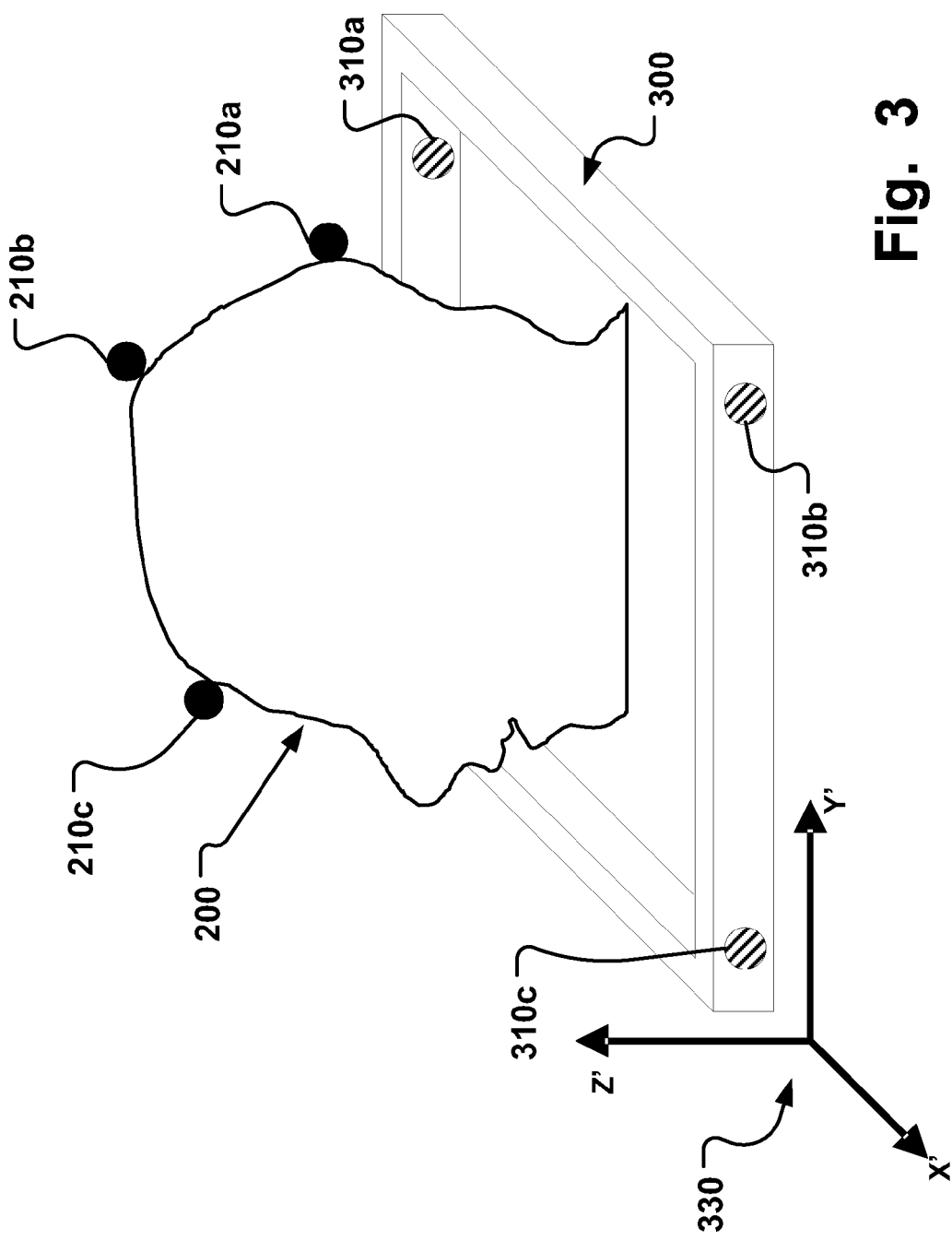
FIG. 3 is a schematic illustration of a stereotactic frame attached to a patient, the stereotactic fiducial markers and a 3D stereotactic coordinate system.

Specific embodiments of the invention will now be described with reference to the accompanying drawings. This invention may, however, be embodied in many different forms and should not be construed as limited to the embodiments set forth herein; rather, these embodiments are provided so that this disclosure will be thorough and complete, and will fully convey the scope of the invention to those skilled in the art. The terminology used in the detailed description of the embodiments illustrated in the accompanying drawings is not intended to be limiting of the invention. In the drawings, like numbers refer to like elements.

The present invention relates to the medical diagnostic and stereotactic surgery arts. The following description focuses on an embodiment of the present invention applicable to stereotactic radiotherapy. However, it will be appreciated that the invention is not limited to this application but may be applied to many other surgery or medical procedures taking advantage of stereotactic localization using a stereotactic frame system. For instance fiducial systems may be positioned in the hip bone and cervix cancer may be treated by a stereotactic surgery system.

In embodiments described below, fiducial markers, visible on e.g. magnetic resonance images are mounted externally on a patient. Three or more fiducial markers are provided for defining a spatial coordinate system.

After an imaging procedure has been carried out, the positions of the fiducial markers in the image volume coordinate system are detected. This is either done manually, or using an automatic or semiautomatic software.

The fiducial markers, or at least an anchoring portion thereof, remain affixed to the patient. The fiducial markers thus remain in a fixed relationship to an anatomical structure at a treatment site. Fixation to a bone structure is preferred.

A stereotactic frame is then fixated to the patient, defining a stereotactic coordinate system. The stereotactic frame is fixated to the patient via arms attached to the fiducial markers. By means of specific arms, as described below, an advantageous, tension free fixation of the frame to the patient is provided. An external device that is configured to externally measure the positions of the fiducial markers and the fixated frame is then used. This measurement procedure is performed on a patient support, which fixates the geometrical relation between the external measuring device and the patient fixated stereotactic frame. Computer software capable of finding the transformation from the fiducial marker positions in the stereotactic frame coordinate system and the fiducial markers in the image volume coordinate system is used. This transformation is used to determine the stereotactic frame system coordinates in the image coordinate system. Computer software capable of synthesizing fiducial markers in the image volume corresponding to the stereotactic frame fiducial system is used.

Stereotactic planning and surgery may be performed using a stereotactic frame system.

With reference to FIG. 1, an embodiment of a method of frameless imaging in a framebased stereotactic surgery system is described. The method 1 comprises the following steps:

100 Positioning of fiducial markers on the patient body;

110 Acquiring patient image data using an image modality;

120 Determining the position of the fiducial markers in a 3D image coordinate system of the acquired image patient data; leaving anchoring units of the fiducial markers in the patient;

130 Affixing a mechanical stereotactic frame to the patient; via arms to the anchoring units of the fiducial markers;

140 Fixating the patient in a patient support with the mechanical stereotactic frame affixed to the patient, wherein the patient support holds an external measurement device;

150 Determining the position of fiducial markers on the patient body and the stereotactic frame in the 3D coordinate system of the mechanical stereotactic frame using the external measurement device;

160 Determining a transformation between the location of the fiducial markers in the coordinate system of the stereotactic frame and the location of the fiducial markers in the 3D image coordinate system;

170 Synthesizing the fiducial marks in the 3D image corresponding to the location of the stereotactic frame fiducial system using the determined transformation; and 180 Performing stereotactic therapy using the stereotactic frame system as a real reference for said therapy.

Thereafter, the frame is detached from the anchoring units. For subsequent therapy sessions, the anchoring units are left on the patient. Steps 130-180 are repeated during a subsequent session. Repeated fixation of fiducial markers, imaging, and therapy planning is not necessary.

Such a method is now elucidated in more detail. Embodiments of fiducial marker systems, stereotactic frames, and systems thereof are elucidated in this connection and in more details are given further below.

100 Positioning of Fiducial Markers on the Patient Body

The first step in the embodiment of the method of frameless imaging in the frame based stereotactic surgery system comprises attaching fiducial markers on anatomically fixed structures of the patient 200.

A fiducial marker is an object that is used in the field of view of an imaging system which appears in the image produced. Fiducial markers may be used to make otherwise invisible or difficult to distinguish features of an image more visible. Fiducial markers may also be used as landmarks, which are identifiable in images taken, and in order to indicate the position thereof in the image. In this manner fiducial markers may act as a reference for image scaling, or may allow the image and physical object, to be correlated with other data in which the position of the fiducial markers also is determinable.

Fiducial markers may for instance be affixed to a bone structure of the patient that substantially is at a defined fixed position in relation to an area to be diagnosed and/or treated. The skull bone is for instance suited for this task with reference to brain structures.

With reference to FIG. 2A, fiducial markers 210a, 210b, 210c are affixed to the patient 200. More precisely, the fiducial markers 210a, 210b, 210c are suitably affixed in a stable manner to a skull bone 202 of the patient 200, for instance preferably by drilling and/or screwing them into the skull bone 202. Alternatively, or additionally the fiducial markers 210a, 210b, 210c may be adhesively affixed. The fiducial markers 210a, 210b, 210c are for instance the fiducial marker system 10 described below with reference to FIG. 8-11, 15 or 17.

However, a balance between being able to remove fiducial markers from the patient and sufficient affixation, even over longer time, without alterations or changes of the position in relation to anatomical fixed structures of the patient has to be taken. Therefore, threaded fixation in a bone structure may be preferred. Threaded affixation may be enhanced by using adhesives, e.g. in a recess receiving the thread of a fiducial marker anchoring unit.

Fiducial markers 210a, 210b, 210c that now are affixed to the patient 200 are provided such that the fiducial markers are identifiable in the image patient data. For instance, the fiducial markers 210a, 210b, 210c may contain a suitable liquid that is excited by an MRI and therefore makes a visible mark in the image volume acquired by an MRI.

In the embodiment described herein, three fiducial markers 210a, 210b, 210c are provided. The absolute number of fiducial markers provided and attached to anatomically fixed structures of the patient may vary and comprise quantities more than three, as long as a defined spatial position of the anatomically fixed patient structure and related anatomical structures of the patient are determinable from the position of detected markers in image patient data. Depending on, for instance, specific patient conditions, specific accuracy requirements, specific measurement systems, specific position detection algorithms used, etc. more than three fiducial markers may be used in embodiments of the system.

Depending on the specific features of a fiducial marker, the mark visible in the acquired images may be visible as a dot, circle, crosshair or more advanced geometry.

Specific embodiments of fiducial markers will be further elucidated below.

110 Acquiring Patient Image Data Using an Image Modality

With continued reference to FIG. 2A and with reference to FIG. 2B, the next step in the embodiment of the method of frameless imaging in the frame based stereotactic surgery system comprises taking the patient with the affixed fiducial markers 210a, 210b, 210c into a image modality and create image patient data.

Suitable image modalities comprise imaging systems such as magnetic resonance imagers (MRIs), computer tomographic imagers (CTs), x-ray imagers, positron emission tomography (PET) scanners, and/or photo-emission computer technology (SPECT). These systems permit physicians to obtain detailed preoperative views of anatomical structures using noninvasive procedures. Once these images are obtained, the physician typically uses the images to plan a corrective surgical procedure.

By means of the image modality image patient data is acquired that covers an entire volume of interest in all three dimensions, including the externally attached fiducial markers 210a, 210b, 210c.

In an embodiment a MRI is used as image modality. The MRI provides image patient data in a plurality of image slices 220. From the image data comprised in each of the image slices 220, three dimensional (3D) image patient data may be obtained by suitable data processing.

In FIG. 2B an image 241 of a single slice 221 is illustrated showing the first visual mark 245a provided by MR scanning of the first fiducial marker 210a.

Magnetic Resonance Imaging is a diagnostic tool considered to be gold standard regarding imaging of soft tissue. Spatial resolution obtained is in the order of one by one by one millimeter in three dimensions and image planes can be oriented freely within the imaged subject.

In the illustrated image 241, the brain structure 244 of the patient's brain 204 is visible inside a virtual skull bone 242 acquired from the patient skull bone 202 in a plane through slice 221.

120 Determining the Position of the Fiducial Markers in a 3D Image Coordinate System of the Acquired Image Patient Data With continuing reference to FIG. 2B, the next step in the embodiment of the method of frameless imaging in the frame based stereotactic surgery system comprises defining the position of each of fiducial markers 210a, 201b, 210c. The location of the fiducial markers fiducial markers 210a, 201b, 210c in the imaged image volume is located and measured in the 3D image volume coordinate system 230.

The exact position of each fiducial marker 210a, 201b, 210c may be found by using a suitable data software that either fully automatically or semi-automatically detects the image mark created by each of the fiducial markers 210a, 201b, 210c. The data software may for instance be based on algorithms detecting the shape and/or pixel intensity of the fiducial marker. The detected positions of the fiducial markers 210a, 201b, 210c may be manually fine tuned. Alternatively, the determination of the position of fiducial markers may be performed manually. However, this needs slice by slice going through the 3D image patient data, which might be rather time consuming.

A center point or point of gravity of each fiducial marker 210a, 201b, 210c is thus determined in the 3D image volume coordinate system 230 (x, y, z). The data program uses e.g. information about pixel intensity and geometrical shape of the fiducial markers to detect the center point of each fiducial marker. All fiducial marker positions are stored in a data memory for later use.

During step 120, the patient may already leave the image modality after image patient data has been acquired. The fiducial marker 210a, 201b, 210c are left stably affixed to the patient. Thanks to a small size, compared to a mechanical frame that conventionally would have been affixed to the patient during an imaging phase of frame based stereotactic surgery, the patient is not heavily burdened by the fiducial markers.

Figure 15:
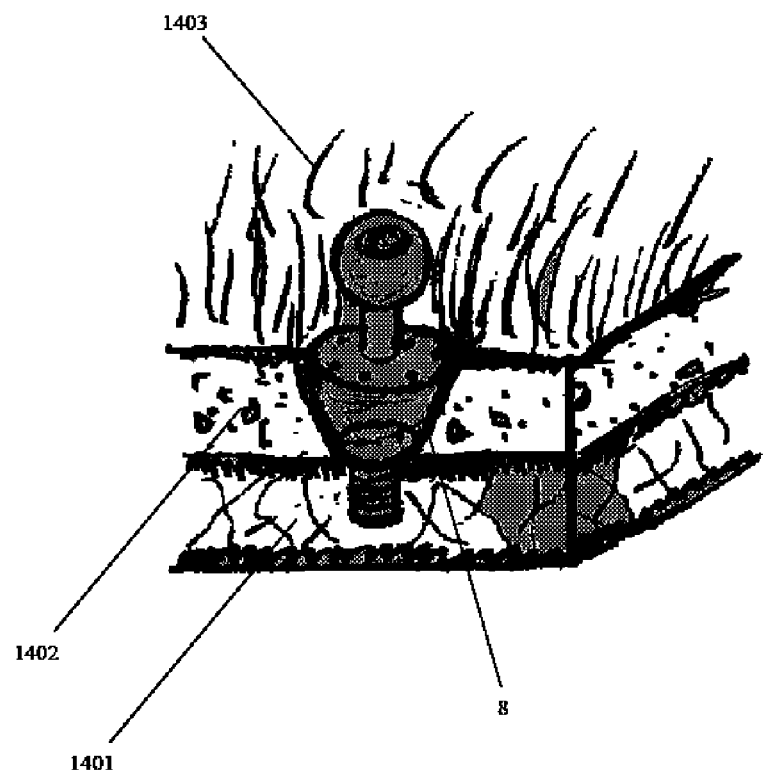
FIG. 15 is a schematic illustration, partly in cross section of an embodiment of a fiducial cup installed in a patient.

Some embodiments of the fiducial markers may even for instance be hidden in the hair of the patient, as illustrated in FIG. 15.

130 Affixing a Mechanical Stereotactic Frame to the Patient

The next step of the embodiment of the method of frameless imaging in the frame based stereotactic surgery system comprises affixing a mechanical stereotactic frame onto the patient 200.

The fiducial markers, or more precisely, first anchoring units thereof with protruding receiving surfaces, are left in place in the patient after step 120. A second unit, used for improving precision of detection of fiducial marker systems is detached from the anchoring units.

Depending on the design of the mechanical stereotactic frame, fixation of the frame to the patient is conventionally done by tensioning pointy screws against a bone structure of the patient 200

For example for a head frame, the screws can be tensioned against the skull bone. A stereotactic frame of the type to be tensioned by means of pointy pins is for instance disclosed in U.S. Pat. No. 5,634,929. However, these frames have a number of drawbacks, for instance that the tensioning mechanically affects the structure of the mechanical frame. Thus the reference provided by the frame is affected likewise when tensioning the latter to the patient.

However, this tensioning is disadvantageous, as describe above. As the fiducial marker units are left in place, these first anchoring units 8 thereof are used as fixation means for the frame via arms, as illustrated e.g. in FIGS. 13A-C. Mounting units 1315 may be provided in the arms, as described below, e.g. with reference to FIGS. 16A-C. The arms are locked in position via lockable joints after attachment to the fiducial anchoring units. This may be done by locking freely pivotable joints. Thus tension free attachment of the frame to the patient is provided. Mounting may be based on force fitting (e.g. clamps) or form fitting (o-ring slid over a spherical head and holding the arms tension free).

The mechanical stereotactic frame 300 comprises predefined surface marks 310a, 310b, 310c, by means of which a stereotactic coordinate system 330 is defined.

140 Fixating the Patient in a Patient Support with the Mechanical Stereotactic Frame Affixed, Wherein the Patient Support Holds an External Measurement Device

Figure 4:
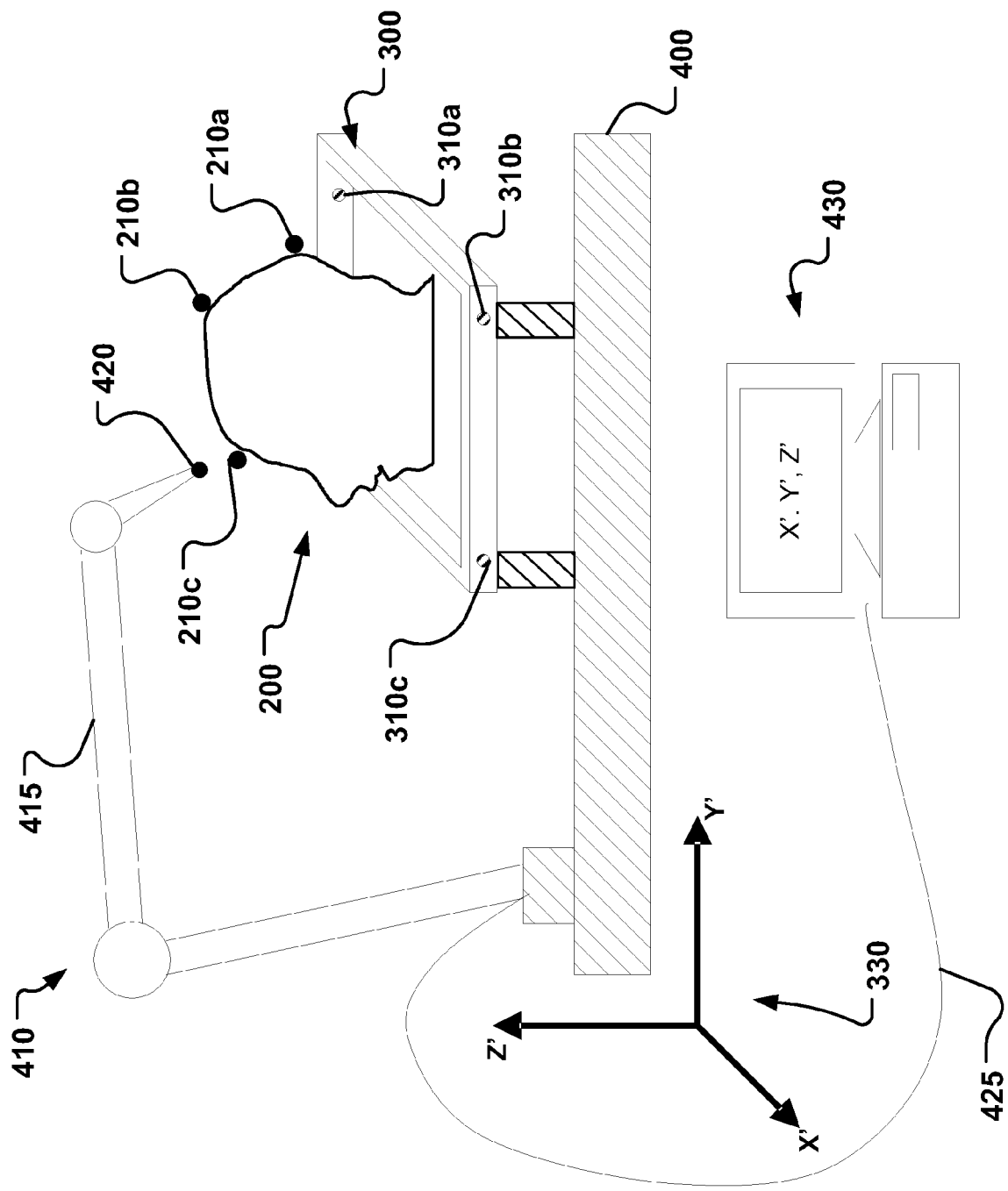
FIG. 4 is a schematic illustration of the fixation of the frame that is affixed to the patient and an external measurement device.

The subsequent step in the embodiment of the method of frameless imaging in the frame based stereotactic surgery system comprises affixing the patient 200 onto a patient support 400, as illustrated in FIG. 4. The patient support 400 provides firm fixation of the mechanical stereotactic frame 300. As the mechanical stereotactic frame 300 is affixed to the patient 200, the patient 200 is provided in a defined spatial position with relation to the patient support 400.

An external measuring device 410 is also fixated to the patient support 400. The external measuring device 410 is thus provided in a defined spatial position with relation to the patient support 400. Moreover the external measuring device 410 is thus provided in a defined spatial position to the mechanical stereotactic frame 300 when affixed to the patient support 400. Furthermore, this defines rigidly defined spatial positions and distances between the fiducial markers 210a, 210b, 210c, the stereotactic frame 300 and its predefined surface marks 310a, 310b, 310c and the external measuring device 410. These rigid positions are all defined in the stereotactic coordinate system 330 (x', y', z').

150 Determining the Position of Fiducial Markers on the Patient body and the Stereotactic Frame in the 3D Coordinate System of the Mechanical Stereotactic Frame Using the External Measurement Device

The embodiment of the method of frameless imaging in the frame based stereotactic surgery system further comprises measuring the positions of the fiducial markers 210a, 210b, 210c and the stereotactic frame 300 in the stereotactic coordinate system 330 (x', y', z'). The fiducial markers 210a, 210b, 210c are measured using the external measuring device 410.

The external measuring device 410 is a device providing accurate data for the spatial position of objects. For instance, a measurement device comprising a measurement arm is commercially available by Faro Technologies Inc. of Lake Mary, Fla. The measurement arm is provided with a plurality of joints that allow endless rotation of the major axis thereof. At an end of the arm a probe is provided. A point in space is measured by positioning the probe on a measurement position. The spatial position of the measurement point is determined, e.g. by highly accurate shaft encoders that allow to compute the position of the probe at any time in 3D space. For instance a measurement precision of approximately ±0.005 mm is achievable in each joint, leading to a total measurement accuracy of the spatial position determined by the measurement point of approximately ±0.05 mm.

In the embodiment such a measurement arm 415 provides spatial data by means of a freely positionable measuring point 420 at the end of the multiple link arm 415. Spatial data of measurement positions is furnished by a suitable computing device 430 of the measurement device 410, which is in communication with the measurement arm 415, e.g. via a line 425.

The spatial position of fiducial markers 210a, 210b, 210c are measured using the external measuring device 410. More precisely, the measurement point 420 is positioned at each of fiducial markers 210a, 210b, 210c affixed to the patient 200. A spatial measurement position of each of fiducial markers 210a, 210b, 210c is recorded and stored in a memory of the computing device 430 for processing.

Likewise, the spatial position of the predefined surface marks 310a, 310b, 310c, by means of which the stereotactic coordinate system 330 is defined, is measured by means of the measurement point 420 being subsequently positioned at each of the predefined surface marks 310a, 310b, 310c. Thus, the position of the mechanical stereotactic frame 300 comprising landmarks in the form of predefined surface marks 310a, 310b, 310c is known. In addition, the position of the patient 200, to which the mechanical stereotactic frame 300 is attached, is known. This is provided thanks to the registered position of the patient affixed fiducial markers 210a, 210b, 210c, or anchoring parts thereof. As the mechanical stereotactic frame 300 is fixed in a spatial relation to the patient affixed fiducial markers 210a, 210b, 210c, the relation between these components and the patient is fixed.

When the measuring point 420 is aligned with one of the fiducial markers 210a, 210b, 210c or one of the predefined surface marks 310a, 310b, 310c on the stereotactic frame 300, the exact position thereof is stored in a memory, e.g. of the computing device 430, in 3D stereotactic coordinates x', y', z' of the stereotactic coordinate system 330. The shape of the measuring point 420 and the topography of the receiving surface of the fiducial markers 210a, 210b, 210c provides that the position of the measuring point 420 exactly correspond to the center point of a fiducial marker 210a, 210b, 210c when a connection between the surfaces of the measuring point 420 and the receiving surface of the fiducial marker 210a, 210b, 210c is made. Embodiments of fiducial markers facilitating such advantageous accuracy and user friendly recording of the spatial position thereof are described in more detail further below in this specification.

160 Determining a Transformation Between the Location of the Fiducial Markers in the 3D Coordinate System of the Stereotactic Frame and the Location of the Fiducial Markers in the 3D Image Coordinate System

Figure 5:
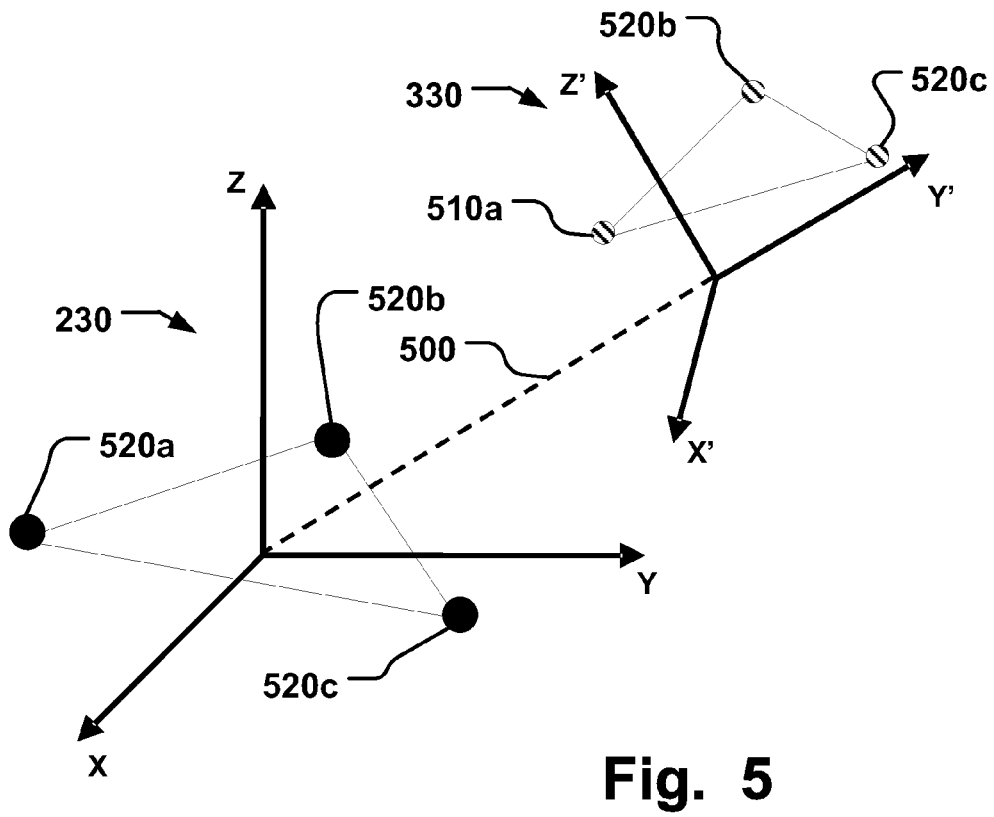
FIG. 5 is a schematic illustration of a transformation from the 3D stereotactic frame coordinate system to the 3D image coordinate system.

The next step in the embodiment of the method of frameless imaging in the frame based stereotactic surgery system comprises finding a geometrical transform between the stereotactic coordinate system 330 (x', y', z') and the 3D image volume coordinate system 230 (x, y, z), as illustrated in FIG. 5. A data software calculates the geometrical transformation 500 between the fiducial marker positions 510a, 510b, 510c in the stereotactic coordinate system 330 and the image coordinate system 230.

The position of each fiducial marker 210a, 210b, 210c is thus defined in both the stereotactic coordinate system 330 and the 3D image volume coordinate system 230.

Figure 6:
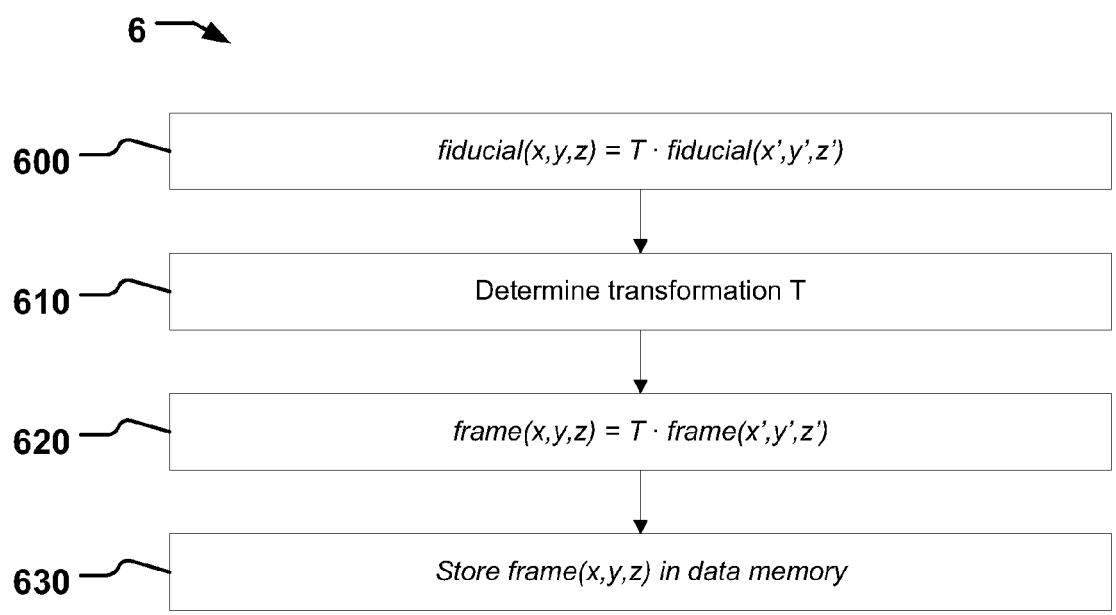
FIG. 6 is a flow chart illustrating a method of transforming the 3D stereotactic frame coordinate system to the 3D image coordinate system.
Figure 7B:
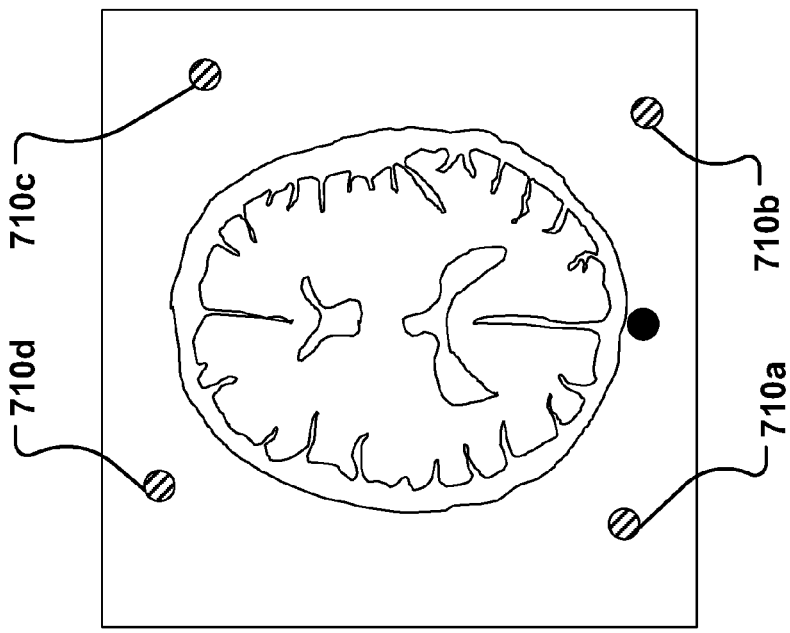
FIGS. 7A and 7B are schematic illustrations of 3D image patient data after synthesized patient fiducial markers and stereotactic fiducial markers.
Figure 7A:
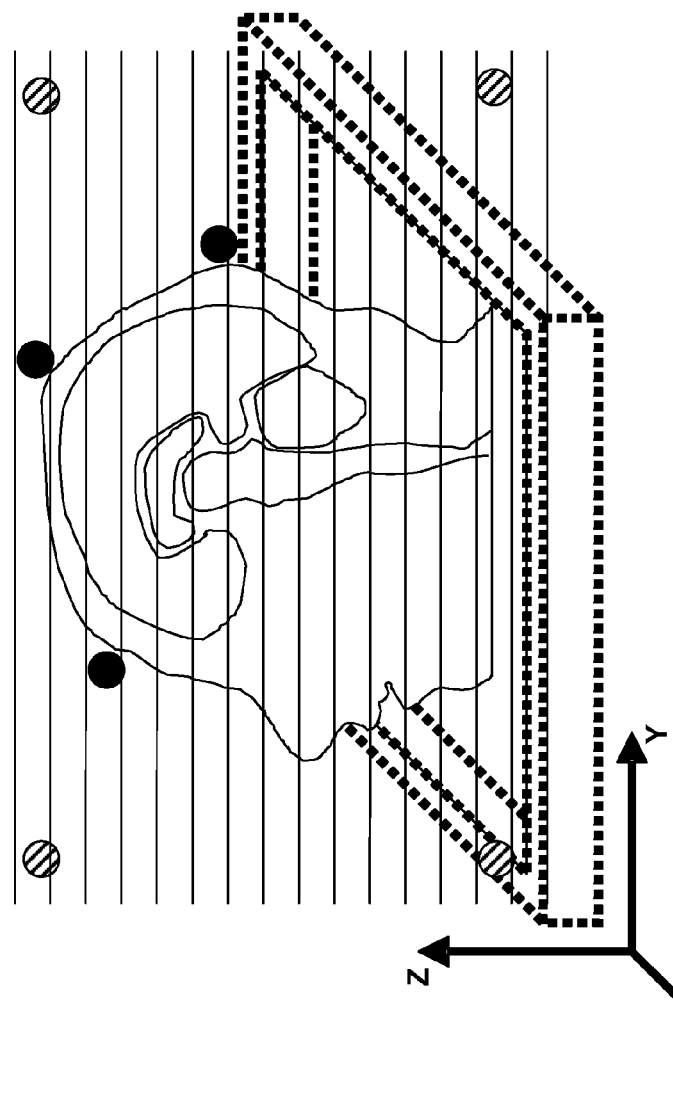

As illustrated in FIG. 6, the transformation (T) may be determined by a method 6, as follows.

In step 600 fiducial($x,y,z$)=$T$·fiducial($x',y',z'$) is determined.

The coordinates for the position of each of fiducial markers 210a, 210b, 210c is known in both coordinate systems. Firstly from the image patient data in the image volume coordinates (x, y, z), and secondly by the measured position in the stereotactic coordinate (x', y', z'). Thus, the transformation T may be determined by the above relation 600. The transformation is found using spatial and rotational operators in step 610.

This means that when a point in 3D space in the stereotactic coordinate system 330 (x', y', z') is multiplied with the transformation T, the coordinates thereof are transformed into image volume coordinates (x, y, z), or vice versa.

Furthermore, the position of the stereotactic frame is known in stereotactic coordinate system 330 (x', y', z'), but unknown in the image volume coordinates (x, y, z). However, the transformation 500 between the two coordinate systems has been determined as T.

Hence, the stereotactic frame's coordinates in the image volume coordinate system 230 are determined in step 620 by applying the transformation T to the stored coordinates of the positions of the frame 300 in the stereotactic coordinate system 330. The result is the coordinates of the frame in the image volume coordinate system 230, which are stored in step 630 in a data memory for future use, e.g. of the computing device 430 or a suitable other workstation, such as a medical workstation. Three or more fiducial markers are used to perform this registration.

170 Synthesizing the Fiducial Marks in the 3D Image Corresponding to the Location of the Stereotactic Frame Fiducial System Using the Determined Transformation In the embodiment of the method of frameless imaging in the frame based stereotactic surgery system, the next step comprises synthesizing fiducial marks in the image volume, corresponding to the position of the stereotactic frame fiducial system 7.

In a visualization used for diagnostics and planning of therapy, pixels corresponding to stereotactic frame positions are manipulated in order to clearly visualize, for instance by altering the pixel intensity such that a differentiation is obtained.

Since step 160 determines the position of the stereotactic frame in the image volume, a plurality of synthesized fiducial marks 710a, 710b, 710c, 710d in the image data volume are generated at known positions with respect to the predefined surface marks 310a, 310b, 310c. These points may be any points inside the imaging volume, as long as their relation to the stereotactic frame is known. This procedure allows for an already existing stereotactic surgery system to recognize these marks and compute the position of the stereotactic frame by only examining the image data volume. Therefore, the synthesized fiducial marks are arranged to have the same position in the image data volume as if a stereotactic frame fiducial system was used during the diagnostic imaging procedure.

E.g. a common way to determine the position of the stereotactic frame in the image data volume, using a conventional frame base stereotactic system, is to attach fiducials to the frame at known positions with respect to the frame.

These fiducials that are attached to the frame are then during surgery planning detected and the position of the frame is calculated. In the present case, the synthesized fiducial marks are placed at these anticipated positions in the image volume, whereby compatibility with existing frame based stereotactic systems is achieved.

The process of synthesizing fiducial marks in the image data volume, may in an embodiment be done by data software, e.g. run on the medical workstation, and the manipulated image volume is saved for future use. Since the image volume may be of limited resolution, e.g. of an MRI scan in the order of one by one by one millimeter, several image pixels close to the actual position of the anticipated fiducial marks have to be manipulated in order to get the center point of the synthesized mark to correspond to the actual position of the frame.

180 Performing Stereotactic Surgery Using the Stereotactic Frame System.

The next step in the embodiment of the method of frameless imaging in the frame based stereotactic therapy system comprises performing stereotactic therapy using the stereotactic frame system 300. Thus, high precision is provided both for the therapy and the registration of patient anatomy, as well as the relation there between.

Based on an analysis of image patient data, a diagnosis of the patient 200 is made. The diagnosis and necessary therapy of a target is virtually planned in the image volume coordinate system 230 (x, y, z). Navigation in the patient 200 during actual surgery is based on the stereotactic coordinate system 330 (x', y', z').

Radiation therapy uses ionizing radiation to kill cancer cells and shrink tumors. Different sources of radiation may be used, for instance X-rays or gamma rays. Therapeutic X-rays may be generated by linear accelerators. Gamma rays are produced when isotopes of certain elements, such as iridium and cobalt 60, release radiation energy as they break down. Each element breaks down at a specific rate and each gives off a different amount of energy, which affects how deeply it can penetrate into the body. Gamma rays produced by the breakdown of cobalt 60 are for instance used by a treatment apparatus known as the "gamma knife,". Alternatively, particle beam radiation therapy may be used for therapy, which use fast-moving subatomic particles. Particle beams may be created by linear accelerators, synchrotrons, or cyclotrons, which produce and accelerate the particles required for this type of radiation therapy. Unlike x-rays and gamma rays, some particle beams can penetrate only a short distance into tissue. Therefore, they are often used to treat cancers located on the surface of or just below the skin.

As mentioned above, stereotactic radiosurgery uses a large dose of radiation to destroy tumor tissue, e.g. in the brain. However, the procedure does not involve actual surgery and is non-invasive. The stereotactic frame 300 is used to aim high-dose radiation beams directly at the tumor inside the patient. The dose and area receiving the radiation are coordinated very precisely based on the previous planning of the therapy. Most nearby tissues are not damaged by this procedure.

Stereotactic radiotherapy uses essentially the same approach as stereotactic radiosurgery to deliver radiation to the target tissue. However, stereotactic radiotherapy uses multiple small fractions of radiation as opposed to one large dose. Giving multiple smaller doses may improve outcomes and minimize side effects. Thus, when fractioning the treatment into a plurality of treatment fractions is facilitated. The frame needs not to remain mounted to the patient for a long time, only during the actual therapy session. A new set of images and target planning is not needed to be performed before each treatment fraction. This makes the improved procedure less expensive, less time consuming, and more patient friendly, in comparison to the state of the art.

Fiducial Marker System

With reference to FIGS. 8 to 12, a fiducial marker system will now be described.

The fiducial marker system comprises two separable units that are releasably attachable to each other.

In an embodiment a first, patient affixable, unit, is provided in the form of a fiducial cup 8 (FIGS. 8A-8D). A second unit is provided, in form of a fiducial disc 9 (FIGS. 9A-9C), that is releasably attachable to the fiducial cup 8.

Figure 17A:
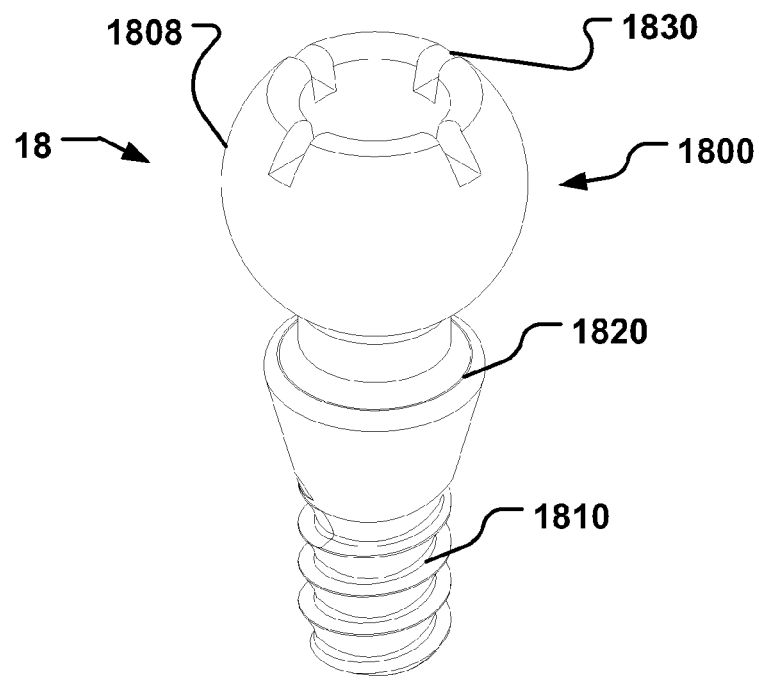
FIGS. 17A and 17B are a perspective view and a lateral cross sectional view of another embodiment of a first, patient affixable, unit of a fiducial marker system.
Figure 17B:
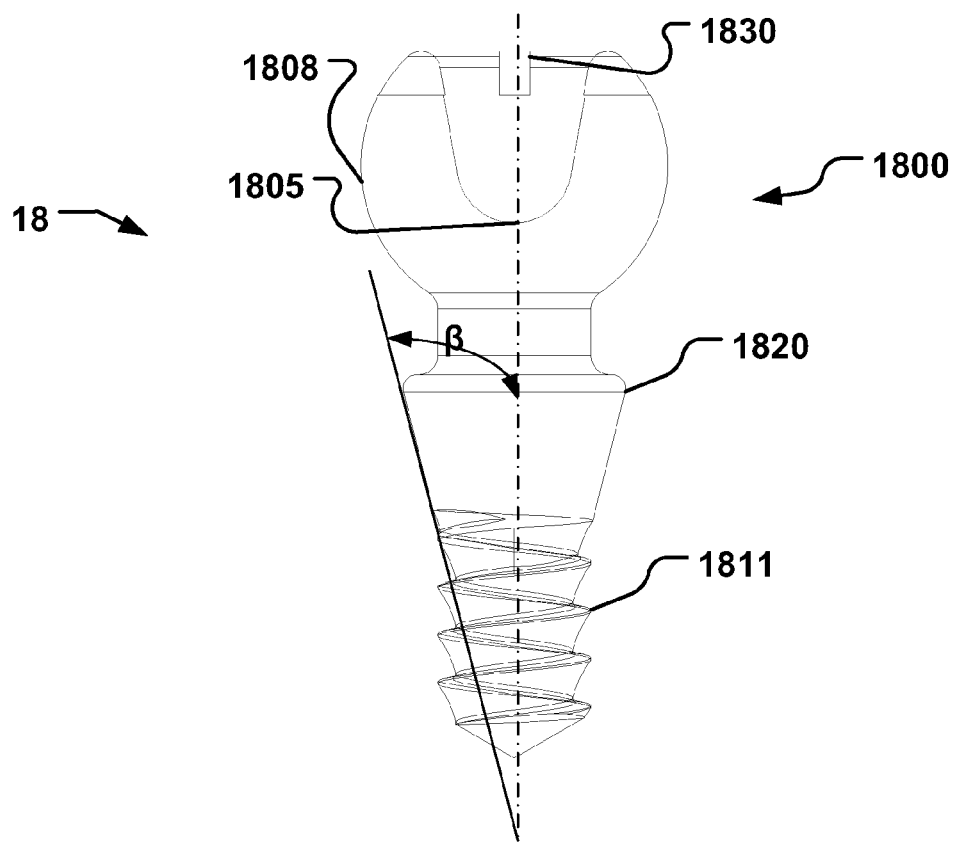

Another embodiment of a first, patient affixable, unit of a fiducial marker system is shown in FIGS. 17A, B and FIG. 15.

A bottom part 810, or anchor part, of the fiducial cup 8 is arranged to be securely attached to the patient, for instance by gluing onto the patients' skin. Gluing may not provide a sufficiently secure attachment, e.g. when having small attachment areas, body hair, etc. Also, long-term attachment may not be sufficient, e.g. for fractionized therapy. Sweat or other body fluids may deteriorate adhesive force of the glue, mechanical wear may occur, etc. In this manner, the fiducial cup may not have the same relation to anatomical structures of the patient after attachment to the patient.

Alternatively, a surgical tool may be used to drill a bore in the patients' bone, wherein the bore is configured to receive the bottom part 810. Alternatively, or additionally, the bottom part 810 may be provided with a helical thread. A helical thread transforms a rotational movement to a translational movement. The bottom part 810 may thus be threadably screwed into a previously prepared bore or directly into the patients' bone for anchoring the fiducial cup in relation to the patient. Alternatively, or additionally, the bottom part 810 may comprise a staple, pin rod, or bone tissue anchor for anchoring the fiducial cup 8 to a patient. The bottom part 810 is thus configured to be releasably anchored or secured in relation to a boney structure such as portions of the skull, or any other boney anatomically fixed structure.

An intermediate portion 820 allows for facilitating the affixing of the fiducial cup 8 and to limit the insertion depth of the fiducial cup in the anatomical structure. In the illustrated embodiment of FIGS. 8A to 8D, the intermediate portion 820 is in the form of a hexagon head that may suitably be rotationally driven by a wrench or a hexagon socket wrench. The rim of the hexagon arranged towards the patient is rounded in order to prevent skin from being injured during the insertion of the fiducial cup 8, as well as when positioned in the patient.

Any dimensions shown in the Figures are purely descriptive, and related to some specific embodiments. Dimensions are not to be interpreted as limiting the invention to these specific dimensions.

Alternatively, or additionally to a hexagon design, other embodiments may comprise a pin socket, or other locking units allowing affixing the fiducial cup 8 to the patient. Some embodiments may even comprise a conical rim that provides a smooth transition when installing the fiducial cup in patient bone tissue. The conical rim, e.g. having a tapering angle β, facilitates insertion of the anchoring part in a recess. Self-centering in the recess is provided. Furthermore, the helical thread of the anchoring unit may be tapered towards the bottom end thereof, located distal of the top portion 800. This may provide for advantageous long-term affixation securing the anchoring part in bone tissue. E.g. FIG. 15 shows the fiducial cup 8 screwed into the cortical bone 1401 using a pin socket wrench. A conical surface on the fiducial cup makes the transition through the patient skin 1402 smooth. The design and/or size of the fiducial cup makes it possible to visibly hide the fiducial cup 8 in the patient hair 1403. This provides for an aesthetic advantage for the patient.

When attached onto the patient, the spatial position of the fiducial cup may be measured with an external measuring device 410, as shown in FIG. 4. By placing the external measuring device's measurement tip 420 into the spherical space 805, as shown in FIG. 8D, inside a hollow of the top portion 800 of the fiducial cup 8. The center of this spherical space 805 inside the hollow of the top portion 800 has substantially the same center point as the at least partly spherical surface 808 on the outside of the top portion 800 of the fiducial cup 8.

As the hollow space has an opening with a larger diameter than the spherical space 805, a secure an easy insertion of the measurement tip 420 into the spherical space is facilitated. The tapered surface between the opening and the spherical bottom, e.g. with a cylindrical transition at a defined tapering angle α, provides a guide surface for the measurement tip 420. The tapering angle α is for instance in the range of 10 degrees, as shown in FIG. 8C.

A fiducial cup 18 shown in FIGS. 17A, B comprises a bottom part 1810, or anchoring part. The anchoring part comprises a helical thread 1811. Recesses or notches 1830 are provided in a partly spherical surface 808. The notches 1830 may receive a tool for rotationally inserting the fiducial cup 18 into bone tissue. Notches 1830 provide for advantageous torque transmission and easy access, both for screwing into and unthreading the fiducial cup 18 from bone tissue. An intermediate portion 1820 allows for limiting the insertion depth of the fiducial cup in the anatomical structure. The intermediate portion 1820 is conical towards the bottom end and has a tapering angle β. The fiducial cup is thus advantageously introduced into a recess in bone tissue, as it provides self centering insertion into the latter. This prevents the patient from being injured during the insertion of the fiducial cup 18, as well as when positioned in the patient. The maximum diameter of the fiducial cup 18 is at the top portion thereof, namely at the partly spherical portion 1808. This facilitates installation with a minimum of space or at difficult accessible anatomical anchoring locations.

Figure 9A:
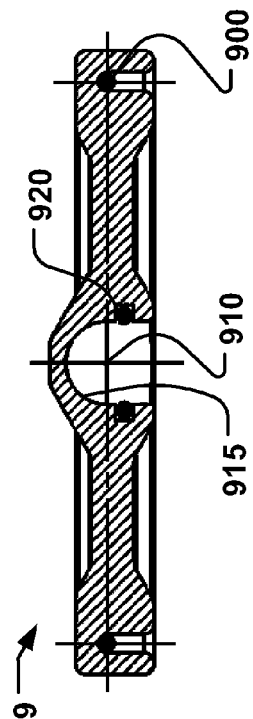
FIGS. 9A to 9C are schematic illustrations of a second, removable, unit of the fiducial marker having two separable units, in the form of a fiducial disc.
Figure 9B:
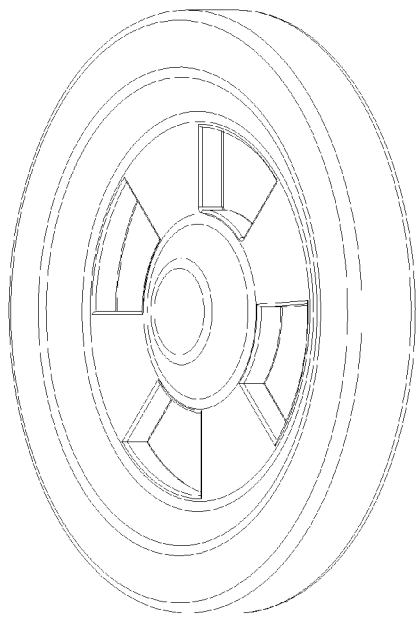
Figure 9C:
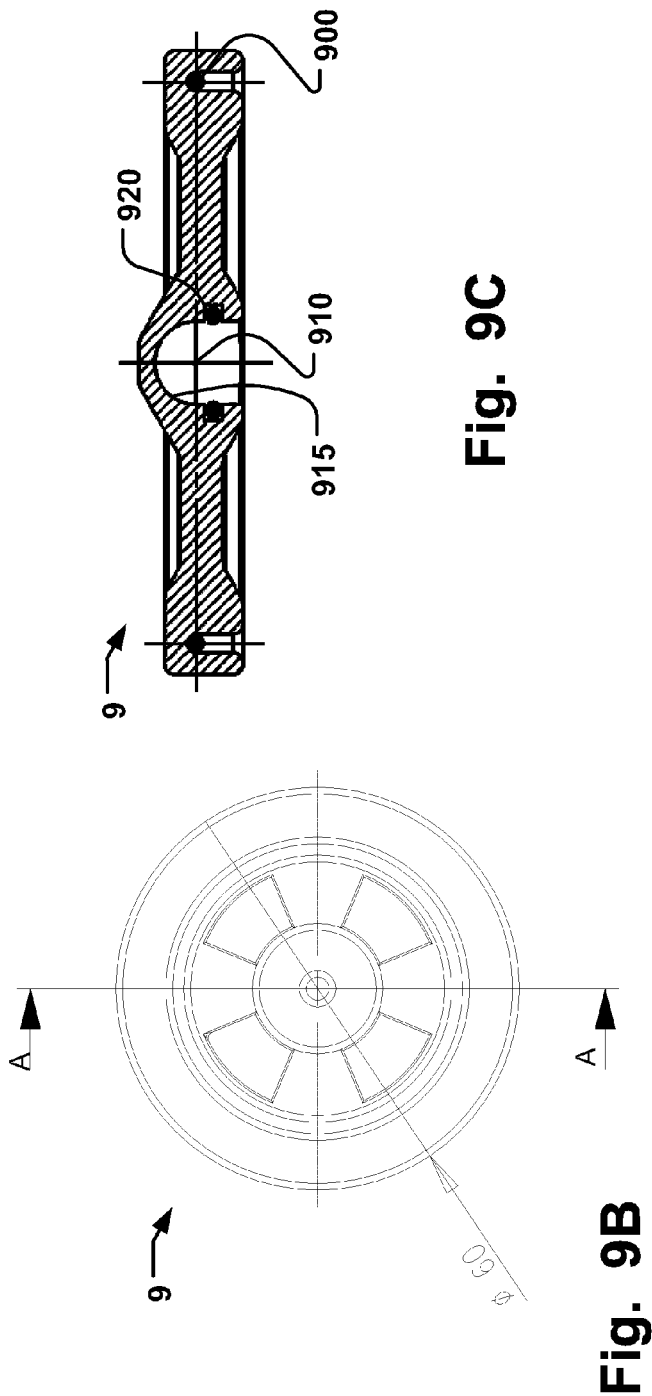

As illustrated in FIGS. 9A-9C, the embodiment of the fiducial disc 9 is a cylindrical member comprising a circular tube 900 and/or recess 920 that comprises radioopaque material, in such a manner that it is identifiable in image data acquired thereof. The cylindrical member has a substantially larger diameter than the diameter of the fiducial cup, e.g. in the range of 5 to 15 times larger, e.g. 10 times larger. The tube 900 is e.g. filled with an agent visible on MRI images or CT images. This circular tube 900 has its center point at the same horizontal coordinate as the center point 910 of the partly spherical surface 915 on the inside of the fiducial disc 9. The radius of the cylindrical tube 900, measured from the center point 910, may vary depending on the imaging procedure chosen, but is in certain embodiments approximately in the range of about 1 cm to about 5 cm, which is substantially larger than the diameter of the fiducial cup 8.

Alternatively, or in addition, to the circular tube 900, the fiducial unit may comprise other radioopaque structures, of which the center point is determinable. These radioopaque structures may in some embodiments even have no continuous, or interrupted, trace, e.g. three radio detectable landmarks, such as spheres, arranged in a defined geometric form, such as an isosceles triangle. Even three-dimensional structures may be provided, such as a partly spherical shape. Here, the center of gravity of the three dimensional structure has to substantially coincide with the center point of the partly spherical surface 808 on the outside of the top portion 800 of fiducial cup 8.

A recess or annular groove 920 may be provided in the fiducial disc 9. The recess 920 is in an embodiment used as a mould for filling a contrast agent therein. The recess 920 is for instance filled with a liquid contrast agent that stiffens, hardens or solidifies in the recess 920. The contrast agent may for instance be water. The contrast agent may be mixed with agarose (polysaccharide obtained from agar) or gelatin. In this manner, a tube 900 is not needed. The fiducial disc 9 is thus advantageously produced with less parts in a less complicated production process. Also, recycling is facilitated when e.g. the hardened contrast agent is re-soluble.

Multiple radioopaque structures, of which the center point is determinable, may be present to further improve detectability and preciseness thereof.

Figure 11C:
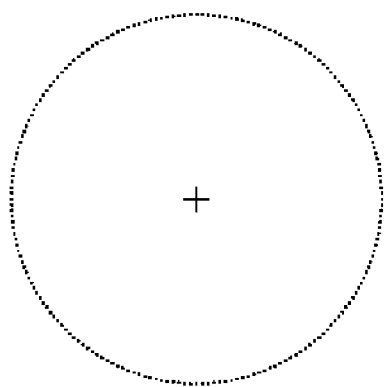
FIGS. 11C, 11D and 11E are two dimensional schematic illustrations of alternative second units of a fiducial marker.
Figure 11D:
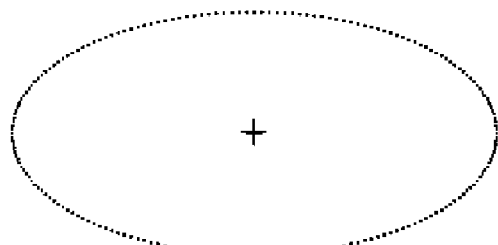
Figure 11E:
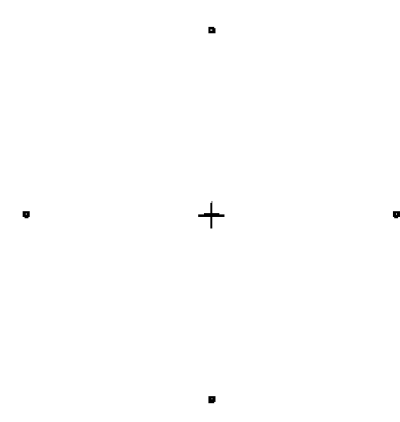
Figure 11F:
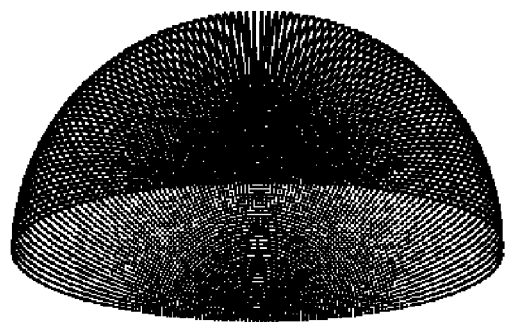
FIG. 11F is a three dimensional schematic illustration of a further alternative second unit of a fiducial marker.

Some examples of alternatively suitable geometries of second units of fiducial markers are given in FIGS. 11C, 11D, 11E and 11F. FIGS. 11C, 11D and 11E are two dimensional schematic illustrations of alternative second units of a fiducial marker. FIG. 11F is a three dimensional schematic illustration of a further alternative second unit of a fiducial marker in accordance with above.

The radius of this partly spherical surface 915 is the same as the partly spherical surface 808 on the outside of the top portion 800 of fiducial cup 8. For assembly purposes, the fiducial disc 9 has an O-ring 920 mounted below the partly spherical surface 915. The O-ring 920 ensures that the fiducial disc 9 may be releasably attached to the top part 800 of the fiducial cup, e.g. during imaging thereof by an imaging modality.

By way of example, the fiducial cup 8 and/or the fiducial disc 9 may be constructed of a plastic material, such as PEEK. PEEK offers in this context the advantage that structures are provideable with high accuracy at a reasonable cost.

Figure 10:
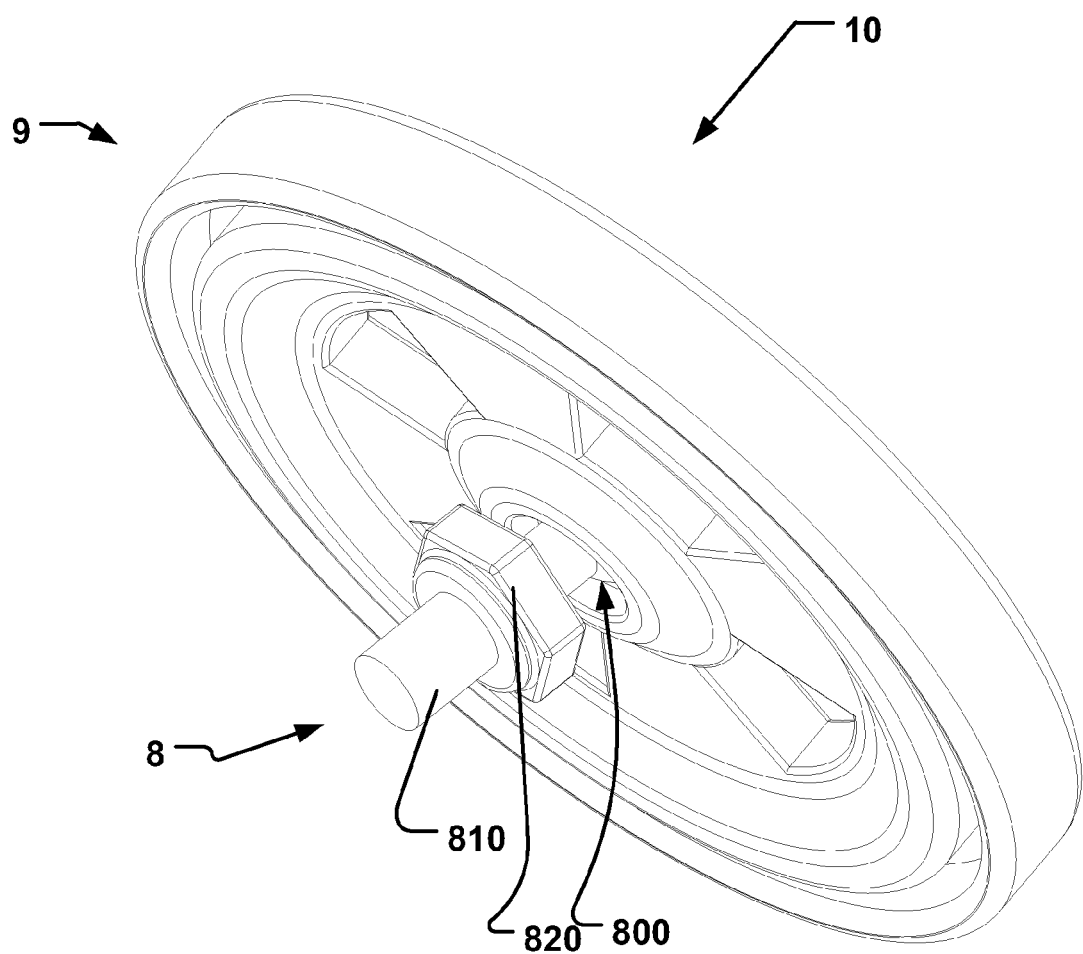
FIG. 10 is a schematic illustration of the fiducial marker, when the two units thereof are assembled.

As illustrated in FIG. 10, the fiducial cup 8 and the fiducial disc 8, may be mounted together into an assembly 10. When mounted together, the O-ring 920 holds the fiducial disc 9 in place, by pressing against the neck of the top portion 800 of fiducial cup 8. The fiducial cup 8 may also be fixated at an inclination angle to the patient's bone. When the fiducial cup 8 and the fiducial disc 9 are assembled, the outer partly spherical surface 808 of the fiducial cup 8 and the mating inner, partly spherical, surface 915 of the fiducial disc 9 connect.

When assembled with the Fiducial cup 8, the fiducial disc 9 may move around the portion 800 of the fiducial disc 8, which itself is attached to the bone of the patient. Disregarding at what angle 11, see FIG. 11B, the fiducial disc 9 is positioned in relation to the longitudinal axis of the fiducial disc 8, the center point of the cylindrical tube 900 and the center point of the partly spherical surface 915 on the inside of the fiducial cup have exactly the same position. This provides an exact registration between the position of the fiducial marker 8, measured with an external arm 415 and by measuring the center point 910 of the trace made in the MRI images, from the agent inside the cylindrical tube 900 or recess 920.

Figure 12:
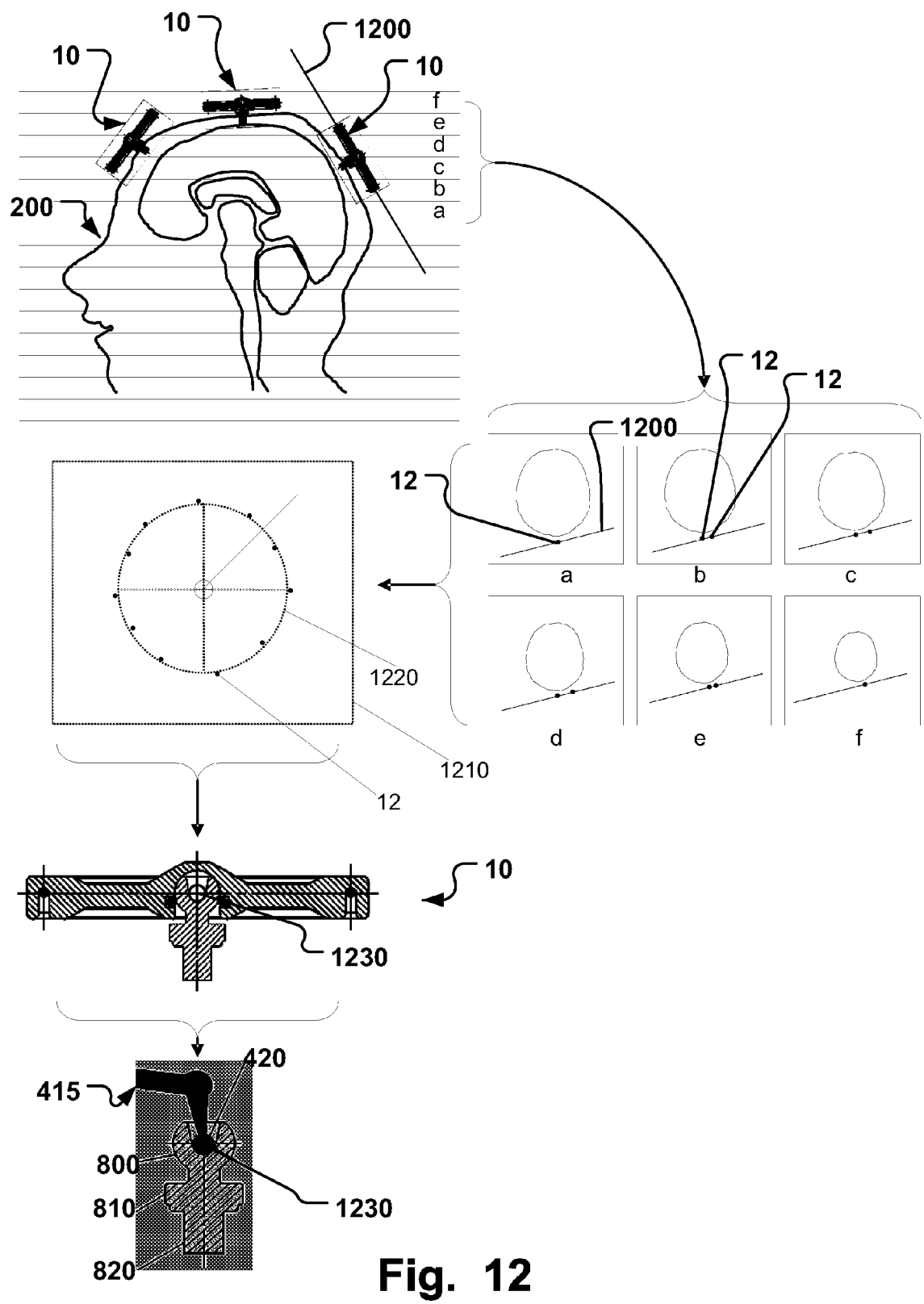
FIG. 12 is a schematic illustration of determining a fiducial marker position in the 3D image coordinate system and the 3D stereotactic coordinate system.

With reference to FIG. 12, determining a fiducial marker position in the image volume coordinate system and the 3D stereotactic coordinate system will now be described.

Patient images using a MR or CT imager are acquired with assemblies 10 of a fiducial cup 8 and a fiducial disc 9 mounted together, and the fiducial cup 8 affixed to the patient 200. Three or more assemblies 10 comprising fiducial markers are used. The agent inside the circular tube 900 or recess 920 will appear as high intensity marks 12 in the images, approximately the size of the diameter of the inside of the circular tube 900 or recess 920.

For example, if an image volume consisted of isotropic voxels with a size of 1 $mm^3$, the radius of the recess 920 and circular tube 900 therein was 25 mm and the diameter of the inside of the circular tube 1 mm. Then, approximately one hundred separated marks 12 in the image volume describe the pattern and position of the circular tube 900. By finding these points 12 and project those onto a circles normal plane 1210, a least square fit to a circle 1220, using these marks 12 may be made. The center of this fitted circle 1220, will correspond to the center point 910 of the fiducial disc 9 and therefore also to the center point 1230 of the fiducial cup 8. Thus, the exact position of the fiducial cup 8 on the patient is determined from image patient data.

The accuracy of this determined position is substantially improved in comparison to identifying the fiducial cup only. Thanks to the removable disc, that is also insensitive to being moved, when connected to the fiducial cup 8, this higher accuracy is achieved. The relatively larger dimension of the fiducial disc 9 compared with the dimension of the fiducial cup 8 provides a large number detectable pixels in the 3D image patient data. The defined geometric relation of this large number of pixels to the center point thereof contributes to the improved accuracy.

The position of the center point 1230 of the fiducial cup 8 may also be located by using an external measuring arm 415, as described above. In this manner the high accuracy coordinates of the center point 1230 of the fiducial cup 8 determined from the image patient data may be registered with the high precision data provided by the measurement arm 415.

In some embodiments, the fiducial first element and/or the second element of the fiducial system disc may be used to attach other equipment than a stereotactic frame. E.g. a high intensity focused ultrasound probe may be releasably attached to the fiducial cups in order to get a fixed relation between the focused ultrasound probe and the relevant target. Furthermore, in embodiments relating to stereotactic surgery or robot assisted stereotactic surgery, surgery tools, such as drills and biopsy needles, may be releasably attached to the fixed fiducial cups, to have a fixed relation between the patient and the surgery tool. The arms that are releasably attachable to the fiducial cups may connect the fiducial cups with other units than a stereotactic frame. For instance, the arms may be fixed to a unit like a surgical tool, a ultrasonic probe, or a biopsy needle. In this manner a defined spatial relationship between the other unit and the fiducial cup is provided.

Frame Unit

FIGS. 13A-13C are schematic illustrations of an embodiment of a stereotactic frame. The stereotactic frame 13 comprises a base frame 1300, which in the embodiment is of rectangular form. A plurality of arms 1310a, 1310b, 1310c, 1310d are mounted to the base frame 1300. At an end portion of the arms a mounting unit is provided that allows for affixing the arms 1310a, 1310b, 1310c, 1310d, and thus the frame 1300 to patient affixable fiducial cups 8a, 8b, 8c, 8d, respectively.

Figures 16A, 16B, 16C:
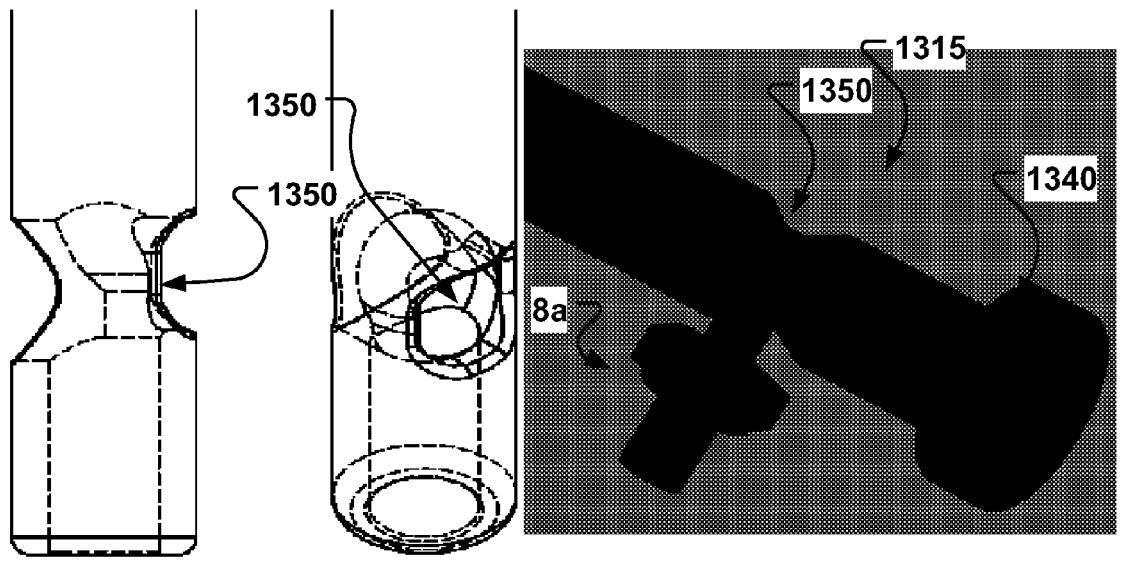
FIG. 16A is a cross sectional view through an end portion of an adjustable arm.
FIG. 16B is an elevated view, partly in section, of the end portion of FIG. 16A.
FIG. 16C is a schematic illustration of the end portion of the arm of FIGS. 16A and 16B affixed to a fiducial cup.

FIGS. 14A to 14C are schematic illustrations of the adjustable arms 1310a of the stereotactic frame of FIGS. 13A-13C. The mounting units of the arms 1310a, 1310b, 1310c, 1310d, as illustrated by the mounting unit 1315, has suitable attachment units that allow affixing the arm to a fiducial cup 8 as described above with reference to FIGS. 8A-8D. The mounting unit is also shown in FIGS. 16A to C. The attachment means 1340 may comprise spring loaded fixation units or releasable attachable units, such as snap locks, or O-ring based constructions such as that of the fiducial disc 9 described above. This is illustrated in FIG. 16C.

Thus, the ends of the arms 1310a, 1310b, 1310c, 1310d may be releasably attached to the fiducial cups 8a, 8b, 8c, 8d. When attached to each other, each or any of the arms may in certain embodiments still freely rotate around a fiducial cup. The arm is thus attached to the fiducial cup, and thus to the patient, without tension that might influence the geometry of the frame. This is advantageous, as for instance accuracy during treatment is maintained.

FIG. 16A is a cross sectional view through an end portion of an adjustable arm; FIG. 16B is an elevated view, partly in section, of the end portion of FIG. 16A. FIG. 16C is a schematic illustration of the end portion of the arm of FIGS. 16A and 16B affixed to a fiducial cup. As can be seen, the end portion of the arm is provided with an opening 1350. The opening allows for access of a measurement arm to the fiducial cup 8, even when the adjustable arm is mounted to the fiducial cup 8. This provides for easy access for measuring the spatial position of the fiducial cup 8, even when the arm, and a corresponding frame or other unit are mounted thereto. In this manner it may for instance be verified that the position of the fiducial cup 8 has not changed. Alternatively, the position of the fiducial cup 8 and related units may be determined by precise measurements after mounting of the two units to each other.

The arms 1310a, 1310b, 1310c, 1310d comprise a plurality of lockable joints, as illustrated in FIG. 14A-C. For instance the arm 1310a comprises two lockable joints 1320a, 1320b. The joints may be freely pivotable joints allowing arbitrary positioning of the arms. When an end of an arm is affixed to a fiducial marker, as described above, the joints may be locked. In this way the frame 1300 is locked in relation to the patient 200 via the locked arms that are affixed to the fiducial cups. The frame is not in mechanical tension when thus being affixed to the patient. Frame tension might otherwise change the geometrical relationship of certain components of the system. For instance, the tension may act upon patient attachment. Patient anchoring units may be relocated, and thus the previously known position of the frame in relation to the patient is no longer valid. Therapy results, which previously may negatively were influenced, are provided more reliably and with improved accuracy over time thanks to the present embodiments.

The frame structure is thus adapted to repeatably and reproducibly fixing the frame to a patient, such as to the head of a patient. Hence, locations within the patient are spatially definable with reference to the frame.

The relocatable frame allows accurate 3-dimensional target localization by CT, MRI, PET and cerebral angiography and precise isocentric positioning for radiotherapy. This method of immobilisation is ideal for fractionated SRT as well as for other techniques requiring high precision localization and treatment delivery.

In another embodiment the frame may comprise a further arm that may be attached to a cervical vertebra, e.g. the spinous process of the vertebra C7.

The frame may be made of a carbon fiber reinforced plastic material in order provide a light weight thereof in combination with high mechanical strength.

The fiducial anchoring units may also comprise a contrast agent, wherein the second unit may be omitted. However, this may lead to reduced precision when detecting the position in space of the fiducial markers.

The present invention has been described above with reference to specific embodiments. However, other embodiments than the above described are equally possible within the scope of the invention. Features of different embodiments may be suitably arranged in order to achieve advantages. Different method steps than those described above, or a different order of said steps as far as feasible, performing the method by hardware or software, etc. may be provided within the scope of the invention. The different features and steps of the invention may be combined in other combinations than those described. The scope of the invention is only limited by the appended patent claims.

The invention claimed is:

1. In a framebased stereotactic therapy system, a fiducial marker system for frameless imaging of a patient comprising a first unit and a second unit, wherein said first unit is patient affixable and configured to be secured directly to a bony anatomical structure of said patient during frameless imaging and framebased stereotactic therapy, and wherein said first unit comprises a partly spherical inner surface having a first center point, which partly spherical inner surface is adapted to receive a touch probe measurement head for measuring said spatial position of said first center point for said framebased stereotactic therapy, and partly spherical outer surface; and wherein said second unit comprises a circular tube filled with an agent detectable by an image modality and has a second center point, wherein said second unit is releasably attachable to said partly spherical outer surface of said first unit such that said first center point and said second center point are substantially identical; and wherein said outer surface of said first unit is configured to releasably receive said second unit for said frameless imaging.

2. The fiducial marker system according to claim 1, wherein said inner surface of said first unit comprises a receiving surface surrounding said first center point of said first unit, and wherein said receiving structure is adapted to receive an external measuring device to measure a spatial position of said first center point by said external measuring device.

3. The fiducial marker system according to claim 1, wherein said position of said circular tube of said second unit has a physical extension such that it is adapted to provide multiple marks in an image volume thereof, wherein said center point of said circular tube is detectable in said image volume by projecting these multiple marks onto a normal plane, whereby said multiple marks are positioned onto a circle, with the same radius as said circular tube.

4. The fiducial marker system according to claim 3, wherein said second unit is rotatable along said outer surface of said first unit and around said first and second center point, such that said center point of said circular tube constantly corresponds substantially to said first center point independent of an angulation of said second unit in relation to a longitudinal axis of said first unit.

5. The fiducial marker system according to claim 1, wherein said agent in said second unit comprises a radioopaque structure.

6. The fiducial marker system according to claim 1, wherein said outer surface of said first unit is releasably attachable to an arm of said framebased stereotactic therapy system for said framebased stereotactic therapy and in such a manner that said first unit is configured to provide a fixed spatial relation between said patient and other equipment of said framebased stereotactic therapy system via said arm.

* * * * *